United States Patent
Kameda

(10) Patent No.: US 6,321,203 B1
(45) Date of Patent: *Nov. 20, 2001

(54) MEDICAL CARE SCHEDULE AND RECORD AIDING SYSTEM AND METHOD

(75) Inventor: Toshitada Kameda, Kamogawa (JP)

(73) Assignee: Kameda Medical Information Laboratory, Chiba-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/158,606

(22) Filed: Sep. 23, 1998

Related U.S. Application Data

(63) Continuation of application No. 08/746,175, filed on Nov. 7, 1996, now Pat. No. 5,913,197.

(30) Foreign Application Priority Data

Dec. 27, 1997 (JP) .................................................. 7-341972

(51) Int. Cl.[7] .................................................. G06F 159/00
(52) U.S. Cl. .................................................. 705/3
(58) Field of Search .................................. 705/1–4, 8–9; 283/2; 707/1, 10, 100–104; 345/440–443

(56) References Cited

U.S. PATENT DOCUMENTS

| 5,072,383 | 12/1991 | Brimm et al. . |
| 5,301,105 | 4/1994 | Cummings, Jr. . |
| 5,325,478 | 6/1994 | Shelton et al. . |
| 5,913,197 | * 6/1999 | Kameda ................................. 705/3 |

FOREIGN PATENT DOCUMENTS

| 62-269534 | 11/1967 | (JP) . |
| 62-245373 | 10/1987 | (JP) . |
| 63-165964 | 7/1988 | (JP) . |
| 4-65771 | 3/1992 | (JP) . |
| 4-333973 | 11/1992 | (JP) . |
| 5-2613 | 1/1993 | (JP) . |
| 5-108677 | 4/1993 | (JP) . |
| 5-143620 | 6/1993 | (JP) . |
| 5-216903 | 8/1993 | (JP) . |
| 6-110947 | 4/1994 | (JP) . |
| 6-259454 | 9/1994 | (JP) . |
| 7-194559 | 8/1995 | (JP) . |
| 7-249085 | 9/1995 | (JP) . |
| 7-249086 | 9/1995 | (JP) . |
| WO 97/06498 | * 2/1997 | (WO) . |

OTHER PUBLICATIONS

Nussbaum, Gerald, "Charting Vital Signs: Computers Boost Patient Care . . .", Corporate Computing, V1, N2, P203(2), Aug. 1992, Dialog File 149, Accession No. 01362788.*

Monthly New Medicine, Jul. 1993, No. 223, pp. 62–64.

Monthly New Medicine, Jul. 1993, No. 223, pp. 44–49.

Japanese Medical Information Association, Lecture Manuscript, pp. 57–60.

P.C. Tang et al., "Semantic integration of information in a physician's workstation", Feb. 1994, pp. 47–60, International Journal of Bio–Medical Computing, vol. 35, No. 1.

Yasushi Horichi et al., "Image Diagnosis and Radioactive Ray Medical Care Series 6th II Examples", Recent Manner to Think and Existence of Radioactive Ray, No. 6, vol. 37, No. 5, Sep. 1995, pp. 483–490.

(List continued on next page.)

Primary Examiner—Frantzy Poinvil
(74) Attorney, Agent, or Firm—Young & Thompson

(57) ABSTRACT

A medical care system includes a first unit with medical care data storage, a first receiving device receiving identification data, a selecting device selecting medical care data related to the patient, and a first transmitting device transmitting selected medical care data to a second unit via the communication line; the second unit with a patient identification data inputting device, a second transmitting device, and an output data generating device generating output data in a table, in which the medical care actions indicated by the received medical care data are arranged in first rows for each type of the medical care actions and in second rows orthogonal to the first rows for each date.

26 Claims, 14 Drawing Sheets

OTHER PUBLICATIONS

Katsuhiro Ohashi et al., "Outpatient Clinic By Use of Electronic Chart", Japan Journal of Medical Informatics, vol. 10, No. 3, Dec. 1990, pp. 227–242.

L. Kleinholz et al., "Supporting Cooperative Medicine: The Bermed Project", Dec. 1994, pp. 44–53, IEEE Multimedia, vol. 1, No. 4.

* cited by examiner

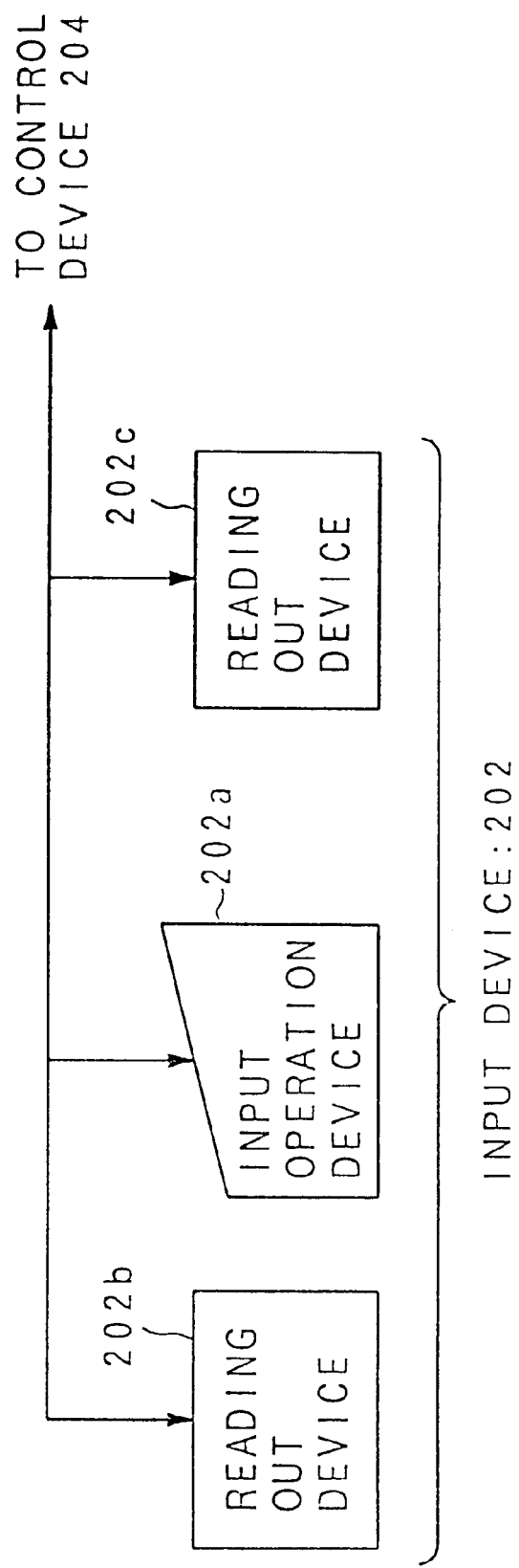

FIG. 4

| | 12-13-94 (Tues)<br>1st DAY (CCU) | 12-14-94 (Wed)<br>2nd DAY (CCU) | 12-15-94 (Thur)<br>3rd DAY (CCU) | 12-19-94 (Mon)<br>7th DAY |
|---|---|---|---|---|
| RECORD | NURSING<br>SCHEDULE | ↓↓ | | ↓↓ |
| ACTIVITY<br>RESTRICTION<br>(REST/EXCRETION/<br>CLEANNESS) | BED BATH<br>PUDIC CLEAN<br>WASH HELPER | BED BATH<br>PUDIC CLEAN<br>WASH HELPER | BED BATH | BED BATH |
| MEAL | | MORNING : ○<br>LUNCH : □<br>DINNER : △ | | ORDINARY MEAL |
| PRACTICE/<br>MONITOR | VITAL SIGN<br>WEIGHT MEASUREMENT<br>SG CATHETER<br>MONITOR CARDIOGRAM<br>PULSE OXIMETER | VITAL SIGN<br>WEIGHT MEASUREMENT | VITAL SIGN<br>WEIGHT MEASUREMENT | VITAL SIGN<br>WEIGHT MEASUREMENT |
| TEST | CARDIOGRAM<br>BREAST X-RAY<br>CPK. CPK-MB<br>24 hours FECALURIA | CARDIOGRAM<br>BREAST X-RAY<br>CPK. CPK-MB<br>24 hours FECALURIA | CARDIOGRAM<br>BREAST X-RAY<br>CPK. CPK-MB<br>24 hours FECALURIA | CARDIOGRAM<br>BREAST X-RAY |
| ORAL MEDICINE/<br>EXTERNAL MEDICINE | | TIMELY<br>ADMINISTRATION 1 | TIMELY<br>ADMINISTRATION 1 | TIMELY<br>ADMINISTRATION 1 |
| INJECTION | INSTILLATION | INSTILLATION | INSTILLATION | INSTILLATION |
| TREATMENT | MT EVULSION<br>S-G EVULSION<br>DIV DELETION<br>WPAPPING<br>NEBIZER<br>SPIRON | A LINE EVULSION<br>B CATH EVULSION<br>NEBIZER<br>SPIRON | Y-DRAIN EVULSION<br>NEBIZER<br>SPIRON | NEBIZER<br>SPIRON |
| | | | | |

FIG. 5

12-09-94 (Fri)  [HOSPITALIZATION 3rd DAY]

◇DOCTOR'S RECORD
　・OPERATION/SURGERY ORDER
◇EVALUATION
　○VITAL SIGN
　○WEIGHT MEASUREMENT
◇MEDICATION
　○06:00　HEPARIN　3000UNITS　DIV
　○12:00　HEPARIN　3000UNITS　DIV
　○18:00　HEPARIN　3000UNITS　DIV
　○24:00　HEPARIN　3000UNITS　DIV
　○TIMELY MEDICATION
　　　: INDERAL TABLET 10mg 3TABLETS
　　　　POSTCIBAL MORNING LUNCH DINNER(UNTIL12.12)

◇TEST
　◎URINE GENERAL TEST
　◎URINE CHEMICAL TEST:CCr
　◎BLOOD SUGAR BURDEN TEST:TRETMENT
　◎15:30　　CC-T　　　　　　(RESERVATION AT HOSPITALIZATION)
　◎PM oncall CAROTID ECHO(RESERVATION AT HOSPITALIZATION)
◇MEAL
　○MEAL INDICATION
　　　: CARDIAC NORMAL FOOD 1600Cal NaC15g
◇REST/EXCRETION/CLEANNESS
　○SHOWER

FIG. 6

| | 12-07-94 (Wed) UPON HOSPITALIZING | 12-08-94 (Thur) 2nd DAY OF HOSPITALIZING | |
|---|---|---|---|
| MEAL | CARDIAC NORMAL FOOD | CARDIAC NORMAL FOOD | |
| TEST | 3 KINDS CULTURE | 9:00 CARDIOGRAM<br>10:00 BREAST X RAY<br>12:00 ANTIBODY TEST<br>15:00 IMA ECHO | |
| | | | |

| | '95 March<br>2 MONTHS<br>LEAVING<br>HOSPITAL | '95 April<br>3 MONTHS<br>LEAVING<br>HOSPITAL | '95 May<br>4 MONTHS<br>LEAVING<br>HOSPITAL |
|---|---|---|---|
| MEDICATION | TIMELY<br>MEDICATION | TIMELY<br>MEDICATION | |
| TEST | March 4th<br>CARDIOGRAM<br>March 18th<br>CARDIOGRAM | April 15th<br>CARDIOGRAM | May 15th<br>CARDIOGRAM |

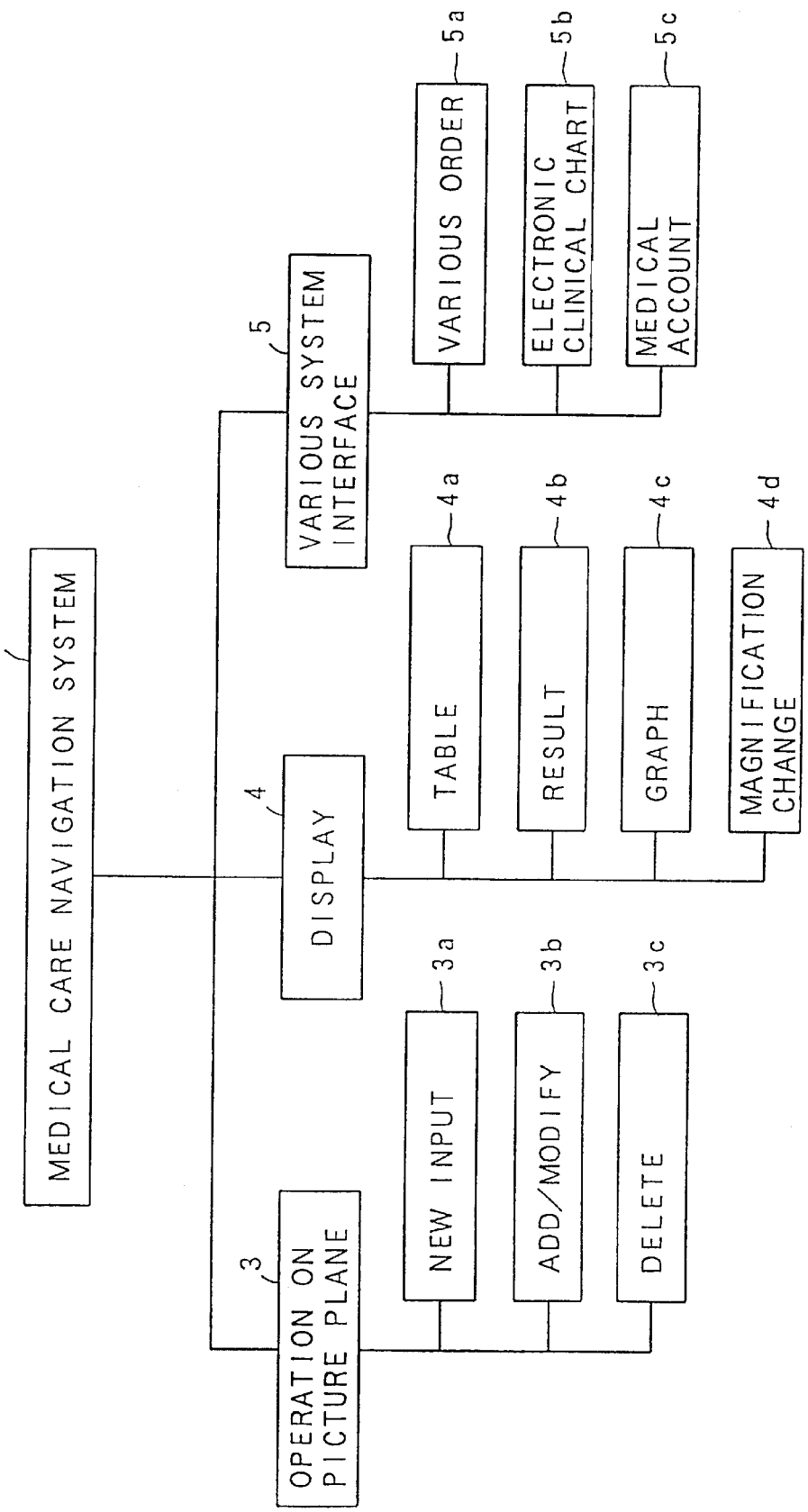

MEDICAL CARE SCHEDULE AND RECORD AIDING SYSTEM AND METHOD

CROSS REFERENCE TO RELATED APPLICATIONS

This application is a continuation of application Ser. No. 08/746,175, now U.S. Pat. No. 5,913,197 filed Nov. 7, 1996, which was refiled as a continued prosecution application on Sep. 22, 1998.

BACKGROUND OF THE INVENTION

1. Field of the Invention

The present invention generally relates to a technical field of managing, storing, processing, inputting and outputting the medical care information, and more particularly to a technical field of a new system for aiding or directing a person related to medical care such as a medical doctor, a nurse, a pharmacist, a medical office worker, a patient and so on, to make up a better medical care schedule and record.

2. Description of the Related Art

Conventionally, each medical doctor, nurse, etc. makes up the medical care schedule as for medical care actions such as a test, an examination, an inspection, a reservation for hospitalizing, an operation, a medication and so on, by thinking and summarizing it in his or her mind on the basis of his or her experience and sense. Therefore, a better medical care schedule can be made up by a well trained medical doctor etc., who carefully considers the needed care.

On the other hand, as a system for processing medical information by use of a computer, there is a computer system for medical office work, to which data indicating types of medical examination, medication, medical insurance etc. are inputted and which speedily calculates the medical care out of those inputted data and outputs a bill. Under the development of the computer communication technique nowadays, an order system is also proposed which quickly transmits the computer readable information in place of a paper chit on which the message is written, from one terminal device at one department to the other terminal device at the other department so as to speed up the preparation of the medicine, the account and the like. Further it has been tried to communicate medical information by use of a personal computer communication such as the internet, the nifty and the like.

Since the medical care schedule is related to a human life and thus very important, it is desirable to standardize the medical care schedule to some extent and keep its quality high, regardless of the discretion or skill of the individual doctor.

However, first of all, the aforementioned medical care schedule, which is made up by each doctor, nurse, etc., needs a means to summarize it to each user in such a way as "the prescription will be performed on X day, the test will be performed on Y day, . . . " for example, which basically cannot function as a schedule table related to the medical care actions or processes. And, above all, this kind of conventional medical care schedule depends very much upon the individual discretion and skill of each doctor, nurse, etc., so that it is almost impossible to schedule and program the medical care processes which are the objectively best in case of serving various medical care actions and processes with respect to numbers of patients who have various kinds of chronic and disease. As a result, there is a serious problem that a less effective medical treatment may be applied by an erroneous judgment of the doctor, the nurse, the pharmacist or the like, and that the condition or disease, which would have been cured by applying the most suitable treatment, is not finally cured. Furthermore, depending upon the type of medical care actions, the medical care schedule may include information, which should be referred to by all of the staff related to the medical care such as the doctor, the nurse, the pharmacist, the medical engineer, the patient himself, the family of the patient, etc., or may include the information which should not be referred to by persons other than the very limited staff. On the other hand, it may be that only limited staff are allowed to make up the schedule, such as only a doctor, only a specialized doctor, only a nurse, only a reservation staff and so on. Accordingly, it requires great effort to make up the medical care schedule, refer to it and change or modify it without any trouble.

On the other hand, the quality itself of the medical care can be hardly improved by the aforementioned computer system for the medical office work and the order system, although the burden on the office works and the waiting time of the patients can be reduced by those systems. Further, according to the aforementioned communication technique for the medical information by use of the personal computer communication, it is still at the stage of transmitting and receiving the computer readable information which content is substantially the same as that of the information written on the paper, and the improvement thereof lies mostly on the high communication speed. Thus, this communication technique works for improving the quality of the medical care in a sense that a doctor may be informed very quickly by chance of a specific medical care method from another doctor who is the personal computer communication colleague. But this communication technique is hardly reliable or useful for scheduling an appropriate, stable and subjective medical treatment processes.

SUMMARY OF THE INVENTION

It is therefore an object of the present invention to provide a medical care schedule and record aiding system, a medical care schedule and record aiding apparatus and a medical care schedule and record aiding method, which can aid or direct the staff relating to the medical care to make up an appropriate and objective medical care schedule and record toward the best medical care for each patient.

The above mentioned object of the present invention can be achieved by a medical care schedule and record aiding system including at least one first unit and at least one second unit connected to each other via a communication line. The first unit is provided with: a medical care data storing device for storing medical care data which indicate a plurality of types of medial care actions with respect to each of a plurality of patients and each date respectively; a first receiving device for receiving patient identification data which indicate one of the plurality of patients via the communication line; a selecting device for selecting the medical care data related to the patient indicated by the received patient identification data; and a first transmitting device for transmitting the selected medical care data via the communication line. The second unit is provided with: an inputting device for inputting the patient identification data; a second transmitting device for transmitting the inputted patient identification data to the first receiving device via the communication line; a second receiving device for receiving the medical care data transmitted from the first transmitting device via the communication line; an output data generating device for generating output data to be graphically outputted in a format of a table, in which the medical care actions indicated by the received medical care data are arranged in first rows for each type of the medical care actions and in second rows orthogonal to the first rows for each date, on the basis of a predetermined format information, which prescribes a framework of the table, and the received medical care data; and an outputting device for graphically outputting the generated output data. The inputting device is constructed to input the medical care data with respect to each patient, each date and each type of the medical care action, the second transmitting device further transmitting the medical care data, inputted by the inputting device, to the first receiving device via the communication line, the first receiving device further receiving the medical care data transmitted from the second transmitting device, the medical care data storing device storing the received medical care data.

According to the system of the present invention, at least one first unit and at least one second unit are connected to each other via the communication line such as a connector cable, a telephone line, an exclusive communication line and the like. The medical care data, which indicate a plurality of types of medial care actions with respect to each of a plurality of patients and each date respectively, are stored by the medical care data storing device provided in the first unit. Here, the "date" may be the date in the past on which each medical care action has been already performed or the date in the future on which each medical care action will be performed. Namely, the "medical care data" indicate at least one of the medical care action which has been already performed in the past and the medical care action which will be performed in the future. The medical care data with respect to "each date" may be with respect to each time of the day in addition to the date, or just with respect to the date having no information as for the time of the day.

Firstly, at the second unit, when the patient identification data are inputted through the inputting device by an operation of the operator such as the doctor, the nurse, the pharmacist, etc., the inputted patient identification data are transmitted from the second transmitting device to the first receiving device via the communication line. Corresponding to this, when the patient identification data indicating an arbitrary one of the plurality of patients are received by the first receiving device via the communication line, the medical care data as for the patient indicated by the received patient identification data are selected from the medical care data storing device by the selecting device. Nextly, the selected medical care data are transmitted by the first transmitting device via the communication line. Corresponding to this, the medical care data transmitted from the first transmitting device are received by the second receiving device via the communication line. Then the output data to be graphically outputted in a format of a table, in which the medical care actions indicated by the received medical care data are arranged in first rows for each type of the medical care actions and in second rows orthogonal to the first rows for each date, are generated by the output data generating device on the basis of the predetermined format information, which prescribes the framework of the table, and the received medical care data. Then, the generated output data are graphically outputted by the outputting device such as the displaying device, the printer and the like. Further, when the medical care data with respect to each patient, each date and each type of the medical care action are inputted through the inputting device by an operation of the operator such as the doctor, the nurse, the pharmacist, etc., the inputted medical care data are further transmitted from the second transmitting device to the first receiving device via the communication line. Then, the transmitted medical care data are received by the first receiving device and the received medical care data are stored by the medical care data storing device. Consequently, the whole staff in the hospital such as the doctor, the nurse, the pharmacist, etc., can watch the same table at once, can share the same information as for the condition of each patient, and can appropriately input the medical care data while watching the table.

In one aspect of the system of the present invention, the second unit is further provided with a format information storing device for storing format information, which prescribes a plurality of formats for graphical output and which includes the predetermined format information prescribing the framework of the table, the inputting device being constructed to specify one of the plurality of formats, the output data generating device generating the output data for graphically outputting the medical care data by the format specified by the inputting device, on the basis of the format information corresponding to the specified format.

According to this aspect of the system, when one of the formats which information are stored in the format information storing device is specified through the inputting device by an operation of the operator, the output data for graphically outputting the medical care data by the specified format are generated by the output data generating device on the basis of the format information corresponding to the specified format. Then, the generated output data are graphically outputted in the specified format of the table by the outputting device. Consequently, a table suitable for the usage circumstance or the usage object of the system can be appropriately displayed and printed on demand, which is very convenient for the various staff in the hospital.

In another aspect of the system of the present invention, the outputting device is provided with a displaying device having a picture plane for displaying the generated output data, the inputting device being constructed to add, change, modify and/or delete the output data displayed on the picture plane of the displaying device, the second transmitting device further transmitting new medical care data corresponding to the output data, which have been added, changed, modified and/or deleted by the inputting device, to the first receiving device via the communication line, the medical care data storing device updating its stored content by the new medical care data received by the first receiving device.

According to this aspect of the system, when the output data displayed on the picture plane of the displaying device are added, changed, modified and/or deleted through the inputting device by an operation of the operator, the new medical care data, which correspond to the added, changed, modified and/or deleted output data, are transmitted by the second transmitting device via the communication line, and are received by the first receiving device. Then, the stored content of the medical care data storing device are updated by the new medical care data received by the first receiving device. Consequently, by such a rather simple input operation that the output data are added, changed, modified and/or deleted on the picture plane by the inputting device on the side of the second unit, the stored content of the medical care data storing device on the side of the first unit can be updated.

In another aspect of the system of the present invention, the outputting device is provided with a displaying device having a picture plane for displaying the generated output data, the inputting device being constructed to specify at least one of an arbitrary date included in a plurality of dates indicated by the output data displayed on the picture plane and an arbitrary type included in a plurality of types indicated by the output data displayed on the picture plane, the output data generating device generating the output data for displaying the medical care data related to the at least one of the date and type specified by the inputting device, in a format different from that of the table, on the basis of the format information corresponding to the different format.

According to this aspect of the system, when at least one of an arbitrary date and an arbitrary type indicated by the output data displayed on the picture plane is specified through the inputting device by an operation of the operator, the output data for displaying the medical care data related to the date and type specified by the inputting device in the format different from that of the table are generated by the output data generating device. Then, the medical care date in the format of, for example, a list which is different from the table is graphically outputted by the outputting device. Consequently, as the operator just specifies the date and/or type by the inputting device, the medical care data related to the specified date and/or type can be graphically outputted in the format different from that of the table e.g. the list, so that various medical care data and various detail medical data can be easily obtained in the graphic output suitable for respective data.

In another aspect of the system of the present invention, the inputting device is constructed to specify the number of dates to be included in one table outputted from the outputting device, the output data generating device constituting at least a portion of the output data to fill each frame of the table by a font, and harmonizing the size of the font to a size of each frame of the table, which is determined by the number of dates specified by the inputting device.

According to this aspect of the system, when the number of dates to be included in one table is specified through the inputting device by the operator, the size of the font is harmonized to the size of each frame of the table which is determined by the specified number of dates, by the output data generating device, which constitutes at least a portion of the output data to fill each frame of the table by the font. Then, the font which has the size harmonized to the size of each frame of the table can be graphically outputted in the table by the outputting device. Consequently, by such a simple operation of merely specifying the number of dates a table, easy to watch in which the font size is suitable for the size of each frame of the table, can be automatically obtained.

In another aspect of the system of the present invention, the inputting device is constructed to input operator identification data for identifying an operator in addition to the patient identification data, the second transmitting device transmitting the operator identification data inputted from the inputting device in addition to the patient identification data, the first receiving device receiving the transmitted operator identification data in addition to the patient identification data, the selecting device selecting only the medical care data indicating the medical care action of a type, which is predetermined as a type able to be referred to with respect to the operator indicated by the received operator identification data, as for the patient indicated by the received patient identification data.

According to this aspect of the system, when the operator identification data for identifying the operator are inputted together with the patient identification data through the inputting device by an operation of the operator, the inputted operator identification data are transmitted with the patient identification data by the second transmitting device, and are received by the first receiving device. Then, only the medical care data indicating the medical care action of the type, which is predetermined as the type able to be referred to with respect to the operator indicated by the received operator identification data, as for the patient indicated by the received patient identification data, are selected from the medical care data storing device by the selecting device. Consequently, the table including only the medical care data of the type set as the type able to be referred to are graphically outputted from the outputting device. Thus, the medical care information can be positively provided to staff of a certain kind and at the same time can be made secret to staff of other kinds, so that the secret information can be prevented from being leaked.

In another aspect of the system of the present invention, the inputting device is constructed to input operator identification data for identifying an operator together with the medical care data, the second transmitting device transmitting the operator identification data inputted from the inputting device with the medical care data, the first receiving device receiving the transmitted operator identification data together with medical care data, the medical care data storing device storing only the received medical care data indicating the medical care action of a type, which is predetermined as a type able to be inputted with respect to the operator indicated by the received operator identification data.

According to this aspect of the system, when the operator identification data for identifying the operator are inputted in addition to the medical care data through the inputting device by an operation of the operator, the inputted operator identification data are transmitted with the medical care data by the second transmitting device, and are received by the first receiving device. Then, only the medical care data indicating the medical care action of the type, which is predetermined as the type able to be referred to with respect to the operator indicated by the received operator identification data, as for the patient indicated by the received patient identification data, are stored to the medical care data storing device. Consequently, the table including only the medical care data of the type set as the type able to be referred to are graphically outputted from the outputting device. Thus, the medical care information as well as the medical care schedule can be added, changed, modified and/or deleted positively by authorized staff. At the same time, it is possible to prevent the medical care data as well as the medical care schedule from being destroyed by unauthorized staff, and it is finally possible to construct the most appropriate medical care schedule in the medical care data storing device by the integration or accumulation of the medical care data inputted in this manner.

In another aspect of the system of the present invention, the inputting device is provided with a reading out device for reading out the patient identification data from a record medium to which the patient identification data are recorded.

According to this aspect of the system, the patient identification data are inputted by the reading out device from the record medium. In this case, as the record medium, a card type medium such as the magnetic card, the IC card, etc. to which the patient identification data are electro-magnetically, magneto-optically or optically recorded, are very useful. As the reading out device, the device for electro-magnetically, magneto-optically or optically reading the data in correspondence with the record medium, can be utilized. The operator identification data may be recorded on and read out from the magnetic card etc. in the same manner as the patient identification data. Further, the patient identification data and the operator identification data may be inputted from the same reading out device. Thus, the patient identification data can be easily read out from the magnetic card, the IC card, etc., which is convenient.

In another aspect of the system of the present invention, the inputting device is provided with a reading out device for reading out the medical care data from a record medium to which the medical care data are recorded.

According to this aspect of the system, the medical care data are inputted by the reading out device from the record medium. In this case, as the record medium, a known large volume data record medium such as the magnetic disk, the optical disk, the ROM, the IC card, the magnetic tape, etc. to which the medical care data for each patient, each date and each type are electro-magnetically, magneto-optically or optically recorded, are very useful. As the reading out device, the device for electro-magnetically, magneto-optically or optically reading the data in correspondence with the record medium, can be utilized. Thus, the medical care data can be easily read out in a large volume from the magnetic disk, the optical disk, etc., which is convenient.

In another aspect of the system of the present invention, the table has a plurality of columns divided by each date and a plurality of lines divided by each type of the medical care action.

According to this aspect of the system, the table having a plurality of columns divided by each date and a plurality of lines divided by each type of the medical care action can be graphically outputted from the outputting device. Thus, the medical treatment process, the program for the medical care schedule, etc. can be easily understood from the table which is very convenient.

In another aspect of the system of the present invention, the types of the medical care actions may include at least one of a medical cure, a treatment, an injection, an examination, a test, an evaluation, a medication, a meal, an activity restriction, an observation, a rehabilitation, a coordination, a hospitalization, leaving the hospital, an education for a family of the patient, a record of a doctor and a record of a nurse.

According to this aspect of the system, the table indicating the various medical care actions is graphically outputted by the outputting device. In this case, the medical care data may be text data expressing each action by the text or code data obtained by coding the content of the medical care action according to a predetermined rule. Thus, it is possible to understand each type of medical care action in association with the date visually at a moment's notice.

In another aspect of the system of the present invention, the second unit is further provided with a counter for counting the date, the output data generating device generating the output data such that one portion of graphical output related to the date corresponding to a present day is displayed in a display manner different from that of the other portions of graphical output, on the basis of the date counted by the counter.

According to this aspect of the system, the date is counted by the counter, and the output data are generated by the output data generating device such that one portion of graphical output related to the date corresponding to a present day is displayed in a display manner different from that of the other portions of graphical output, on the basis of the date counted by the counter. Here, the different display manner may be such a display manner that the color, the brightness, the styles, the kind of lines, the concentration, the half tone meshing, etc. may be changed on the displayed image. Consequently, the table in which one portion of graphical output corresponding to the present day is displayed in the different display manner is outputted by the outputting device. Thus, it is possible to visually recognize at a moment's notice where is the present day i.e. up to which date the medical care treatment has been performed at the present time in the table in which the items are arranged for each date.

In another aspect of the system of the present invention, a result flag indicating whether or not the medical care action has been already performed is attached to the medical care data, the output data generating device generating the output data such that one portion of graphical output related to the medical care action which has been already performed is displayed in a display manner different from that of another portion of graphical output related to the medical care action which has not been performed yet, on the basis of the result flag.

According to this aspect of the system, the output data are generated by the output data generating device on the basis of the result flag such that one portion of graphical output related to the medical care action which has been already performed is displayed in a display manner different from that of another portion of graphical output related to the medical care action which has not been performed yet. Consequently, the table by which it is possible to visually recognize at a moment's notice whether or not each medical care action has been performed can be graphically outputted by the outputting device. Further, it is also possible to visually recognize whether or not the detail medical data indicating the result of the medical care action exist logically under the medical care data, which is very convenient.

In another aspect of the system of the present invention, at least one of the second units may be a unit for medical examination which is provided with an output data generating device for generating the output data for graphically outputting a medical examination report by use of the medical care data received by the second receiving device.

According to this aspect of the system, the output data for graphically outputting the medical examination report can be generated by the output data generating device, and the medical examination report is outputted by the outputting device in the unit for medical examination. Thus, this unit for medical examination adapted to output the medical examination report as well as the table is very useful as the unit for the medical doctor who actually performs the medical examination.

In another aspect of the system of the present invention, at least one of the second units may be a unit for accounting which is provided with an output data generating device for further performing a calculation for medical care accounting by use of the medical care data received by the second receiving device and generating the output data for graphically outputting a medical care account record on the basis of a calculation result.

According to this aspect of the system, the calculation for medical care accounting is performed by use of the received medical care data and the output data for graphically outputting the medical care account record are generated on the basis of the calculation result. Thus, the medical care account record is graphically outputted by the outputting device in the unit for accounting. Thus, this unit for accounting is very useful as the unit for the office workers for executing the accounting.

In another aspect of the system of the present invention, at least one of the second units may be a pharmaceutic unit which is provided with an output data generating device for generating the output data for graphically outputting a medicine list by use of the medical care data received by the second receiving device.

According to this aspect of the system, the output data for graphically outputting a medicine list by use of the received medical care data are generated by the output data generating device. Consequently, the medical list is graphically outputted by the outputting device in the pharmaceutic unit. Thus, this pharmaceutic unit for outputting the medicine list as well as the table is very useful as the unit for the pharmacist or the worker for delivering the medicine.

In another aspect of the system of the present invention, the medical care data storing device stores at least one portion of the medical care data for each time of the day in addition to the date, the output data generating device generating the output data for graphically outputting the medical care data such that the medical care actions are arranged per each time of the day in each frame of the table as for the at least one portion of the medical care data, on the basis of the medical care data for each time of the day.

According to this aspect of the system, the output data generating device generating the output data for graphically outputting the medical care data such that the medical care actions are arranged per each time of the day in each frame of the table as for the stored portion of the medical care data, are generated by the output data generating device on the basis of the medical care data for each time of the day which are stored in the medical care data storing device. Consequently, the table in which the medical care actions are arranged per each time of the day in each frame is graphically outputted from the outputting device. Thus, the timely arrangement of each medical care actions in each frame of the table can be visually understood at a moment's notice.

In another aspect of the system of the present invention, the medical care data storing device stores at least one portion of the medical care data for each time of the day in addition to the date, the output data generating device generating the output data for graphically outputting the medical care data such that the medical care actions are arranged in the table divided into each predetermined time interval instead of each date, as for the at least one portion of the medical care data, on the basis of the medical care data for each time of the day.

According to this aspect of the system, the output data for graphically outputting the medical care data such that the medical care actions are arranged in the table divided into each predetermined time interval instead of each date, as for the at least one portion of the medical care data, are generated by the output data generating device on the basis of the medical care data for each time of the day. Consequently, the table divided into each predetermined time interval such as 6 hours, 12 hours or the like is graphically outputted by the outputting device. Thus, the table is useful in case of making up a fine medical care schedule with respect to each time of the day e.g. in the case of the schedule for the hospitalization.

In another aspect of the system of the present invention, the output data generating device generates the output data for graphically outputting the medical care data in a format of a table in which the medical care actions are arranged in the second rows for each predetermined consecutive dates instead of each date, as for at least one portion of the medical care data.

According to this aspect of the system, the output data for graphically outputting the medical care data in the format of the table in which the medical care actions are arranged in the second rows for each predetermined consecutive dales are generated by the output data generating device, as for at least one portion of the medical care data. Consequently, the table in which the medical care actions are arranged in the second rows for each predetermined consecutive dates such as one week, one month or the like is graphically outputted by the outputting device. Thus, the table is useful in case of watching the medical care action which is performed at the time far from the time of the hospitalization in one table, for example.

In another aspect of the system of the present invention, the first unit is further provided with: the inputting device; the output data generating device; and the outputting device, the first transmitting device and the first receiving device functioning as the second transmitting device and the second receiving device respectively, and the second unit is further provided with: the medical care data storing device; and the selecting device, the second transmitting device and the second receiving device functioning as the first transmitting device and the first receiving device respectively, the first and second units each having a construction same to each other.

According to this aspect of the system, the same table outputted by the outputting device and the medical care data are inputted by the inputting device in each of the first and second units. Thus, the medical care schedule and record aiding system can be constructed by use a plurality of personal computers of the same kind connected in one network, which is convenient in a medical practice. Instead, the first unit may be one central unit, which is provided with a large data volume storing device and is connected with the second unit, while the second unit maybe a terminal device for individual use which is rather simply constructed without large data volume storing device.

In another aspect of the system of the present invention, the medical care data storing device further stores detail medical data related to the medical care action indicated by each medical care data, in connection with each medical care date, the selecting device selecting the detail medical data as for the patient indicated by the received patient identification data together with the medical care data, the first transmitting device transmitting the selected detail medical data together with the medical care data via the communication line, the second receiving device receiving the detail medical data transmitted from the first transmitting device together with the medical care via the communication line, the inputting device being constructed to specifying desirable ones of the medical care data among the medical care data outputted as the table by the outputting device, the output data generating device generating the output data for graphically outputting the detail medical data related to the desirable one of the medical care data specified by the inputting device in a predetermined format different from that of the table, on the basis of the detail medical data.

According to this aspect of the system, the detail medical data related to each medical care action are stored in the medical care data storing device in connection with each medical care date. The detail medical data as for the patient indicated by the received patient identification data together with the medical care data are selected by the selecting device, and are transmitted by the first transmitting device. Then, the selected detail medical data together with the medical care data are received by the second receiving device via the communication line. At this stage, when the desirable one of the medical care data is specified through the inputting device by an operation of the operator among the medical care data outputted as the table by the outputting device, the output data for graphically outputting the detail medical data related to the specified desirable one of the medical care data in the predetermined format different from that of the table, are generated by the output data generating device on the basis of the detail medical data. Consequently, the detail medical data related to the specified desirable one of the medical care data are graphically outputted by the predetermined format by the outputting device. Thus, as the operator such as the doctor, the nurse, the pharmacist etc. just specifies the desirable one of the medical care actions indicated in the table, the detail medical data can be graphically outputted in the display format different from the table or in the window picture plane, which is very advantageous from a view point of dealing with various data in the limited picture plane area.

In this aspect of the present invention, the format information storing device may store the format information, which prescribes a plurality of formats for graphically outputting the detail medical data such as the list, the graph, the chart, etc., and the output data for graphically outputting the detail medical data by the specified format may be generated by the output data generating device when one of the plurality of formats is specified by the inputting device, so that the list, the graph, the chart, etc. can be outputted in place of the table. Alternatively, in this aspect of the present invention, the output data for graphically outputting the list, the graph, the chart, etc. may be generated by the output data generating device by use of the detail medical data related to the date and/or type specified by the inputting device on the picture plane of the displaying device as the outputting device, so that the operator can specify and call the detail medical data related to the medical care action while watching the medical care action in the displayed table, according to circumstances.

In another aspect of the system of the present invention, the detail medical data include numerical data, which are related to a predetermined type of the medical care action and are recorded with respect to a plurality of dates, the output data generating device generating the output data for graphically outputting the table at one portion of an output image and further generating the output data for graphically outputting the numerical data as a graph having a time axis corresponding to an arrangement of the dates of the table at another portion of the output image on the basis of the numerical data.

According to this aspect of the system, the output data for graphically outputting the table at one portion of the output image and the output data for graphically outputting the numerical data as a graph having a time axis corresponding to an arrangement of the dates of the table at another portion of the output image are generated by the output data generating device on the basis of the numerical data. Consequently, the numerical data are graphically outputted as the graph having the time axis together with the table in the same picture plane, by the outputting device. Thus, the relationship between the medical care actions which have been performed and the numerical data which indicate the condition of the patient can be visually understood.

The above mentioned objects of the present invention can be achieved by a medical care schedule and record aiding apparatus, which is connected via a communication line to a medical care center unit provided with: a medical care data storing device for storing medical care data, which indicate a plurality of types of medial care actions with respect to each of a plurality of patients and each date respectively; a first receiving device for receiving patient identification data which indicate one of the plurality of patients via the communication line, and further receiving the medical care data to be stored into the medical care data storing device via the communication line; a selecting device for selecting the medical care data related to the patient indicated by the received patient identification data; and a first transmitting device for transmitting the selected medical care data via the communication line. The apparatus is provided with: an inputting device for inputting the patient identification data and the medical care data with respect to each patient, each date and each type of the medical care action; a second transmitting device for transmitting the inputted patient identification data and the inputted medical care data to the first receiving device via the communication line; a second receiving device for receiving the medical care data transmitted from the first transmitting device via the communication line; an output data generating device for generating output data to be graphically outputted in a format of a table, in which the medical care actions indicated by the received medical care data are arranged in first rows for each type of the medical care actions and in second rows orthogonal to the first rows for each date, on the basis of a predetermined format information, which prescribes a framework of the table, and the received medical care data; and an outputting device for graphically outputting the generated output data.

According to the apparatus of the present invention, the advantageous effect same as that of the aforementioned system of the present invention can be achieved.

The above mentioned objects of the present invention can be achieved by a medical care schedule and record aiding method for a medical care schedule and record aiding apparatus, which is connected via a communication line to the above described medical care center unit. The method includes the steps of: transmitting the patient identification data, which are inputted by an inputting device for inputting the patient identification data, to the receiving device via the communication line; receiving the medical care data transmitted from the transmitting device via the communication line; generating output data to be graphically outputted in a format of a table, in which the medical care actions indicated by the received medical care data are arranged in first rows for each type of the medical care actions and in second rows orthogonal to the first rows for each date, by an outputting device on the basis of a predetermined format information, which prescribes a framework of the table, and the received medical care data; and transmitting the medical care data with respect to each patient, each date and each type of the medical care action, which are inputted by the inputting device, to the receiving device via the communication line.

According to the method of the present invention, the same advantageous effects as that of the aforementioned system of the present invention can be achieved.

The above mentioned objects of the present invention can be achieved by a program storage device readable by a medical care schedule and record aiding apparatus, tangibly embodying a program of instructions executable by the medical care schedule and record aiding apparatus to perform method steps for aiding in the preparation of a medical care schedule and record. The medical care schedule and record aiding apparatus is connected via a communication line to the above described medical care center unit. The method steps comprise: transmitting the patient identification data, which are inputted by an inputting device for inputting the patient identification data, to the receiving device via the communication line; receiving the medical care data transmitted from the transmitting device via the communication line; generating output data to be graphically outputted in a format of a table, in which the medical care actions indicated by the received medical care data are arranged in first rows for each type of the medical care actions and in second rows orthogonal to the first rows for each date, by an outputting device on the basis of a predetermined format information, which prescribes a framework of the table, and the received medical care data; and transmitting the medical care data with respect to each patient, each date and each type of the medical care action, which are inputted by the inputting device, to the receiving device via the communication line.

According to the program storage device of the present invention, the same advantageous effects as that of the aforementioned system of the present invention can be achieved.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

FIG. 3 is a block diagram showing a detailed construction of an input device of the first embodiment;

FIG. 4 is a plan view showing one example of a table which is graphically outputted by the first embodiment;

FIG. 5 is a plan view showing one example of a list which is graphically outputted by the first embodiment;

FIG. 6 is a plan view showing another example of a table which is graphically outputted by the first embodiment;

FIG. 16 is a diagram showing functions of the medical care navigation system of the embodiments.

DETAILED DESCRIPTION OF THE PREFERRED EMBODIMENTS

Referring to the accompanying drawings, embodiments of the present invention will be now explained.

1. First Embodiment

Figure 1:
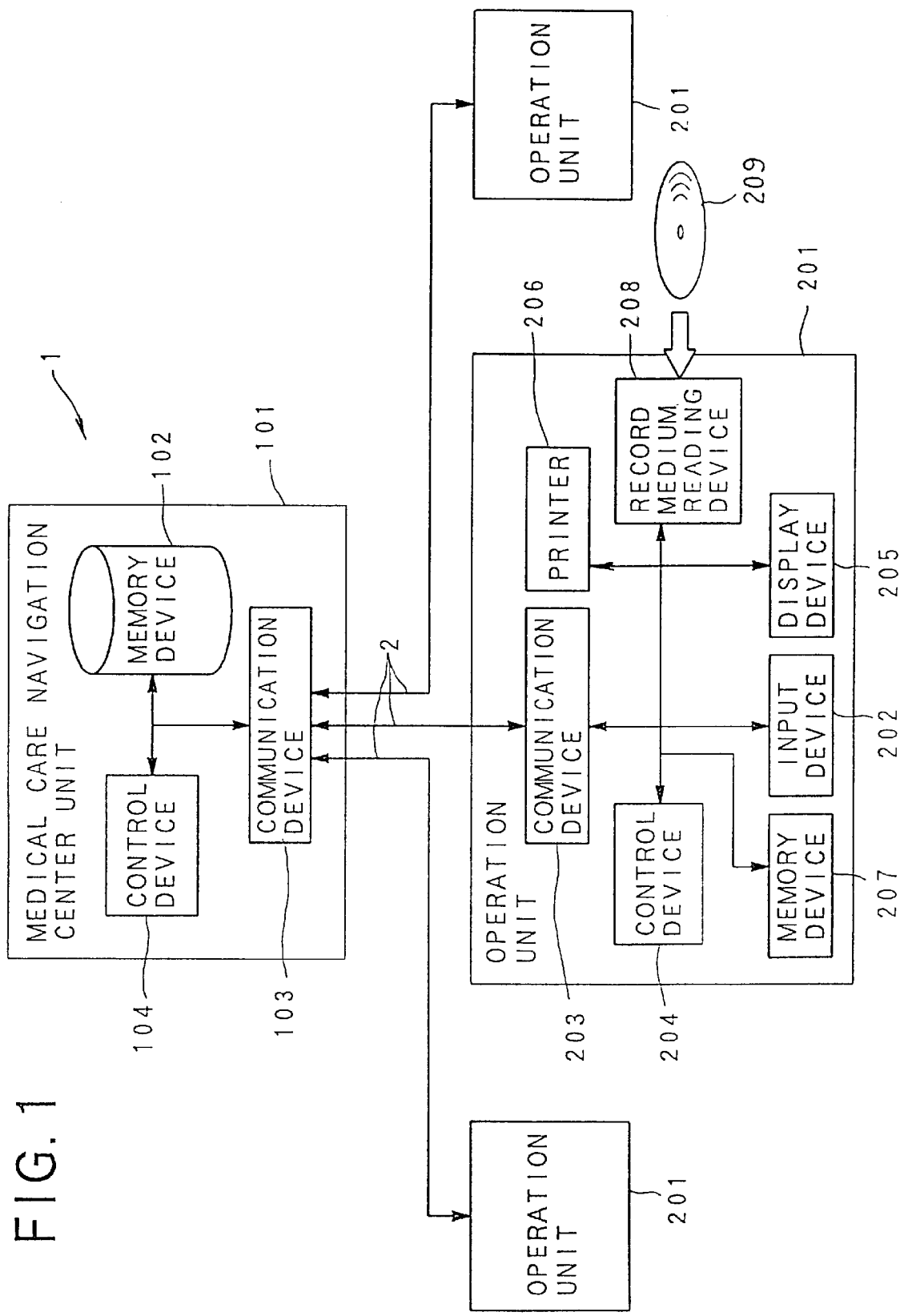
FIG. 1 is a block diagram of a medical care navigation system as a first embodiment of the present invention.

FIG. 1 shows a block diagram of a medical care navigation system for navigating the staff in the hospital e. g. the doctor, the nurse, the pharmacist as well as the patient to the appropriate medical care, as an example of the medical care schedule and record aiding system of an first embodiment of the present invention.

In FIG. 1, a medical care navigation system 1 is provided with a medical care navigation center unit 101, and a plurality of medical care navigation operation units 201 which are connected to the center unit 101 via a communication line 2.

The center unit 101 is provided with: a memory device 102 for storing medical care data which indicate medical care actions of various types with respect to each of a plurality of patients at least per date as the time information when each medical care action is to be performed; a communication device 103 for receiving various data e.g. patient identification data, which indicate one of a plurality of patients, medical care data; and a control device 104 for selecting the medical care data corresponding to the patient, who is indicated by the received patient identification data, from the memory device 102. The communication device 103 also transmits the selected medical care data onto the communication line 2.

Each of the operation units 201 is provided with: an input device 202 for inputting various data e.g. the patient identification data, and the medical care data; a communication device 203 for transmitting the patient identification data, etc. to the communication device 103 via the communication line 2, and for receiving the medical care data transmitted from the communication device 103 via the communication line 2; a control device 204 for generating output data to graphically output the medical care data, which are received by the communication device 203, as a table in which the medical care actions of various types are arranged for each type of action and each date, on the basis of predetermined format information prescribing the format of the table; a memory device 207 for storing the predetermined format information; a display device 205 for displaying the generated output data; and a printer 206 for printing the generated output data.

The input device 202 is constructed such that the medical care data can be inputted therethrough for each patient, each data and each type of action, separately. The communication device 203 is adapted to transmit the medical care data inputted through the input device 202 to the communication device 103 via the communication line 2. On the other hand, the communication device 103 is adapted to receive the transmitted medical care data, and the memory device 102 is adapted to store the received medical care data under the control of the control device 104.

Each operation unit 201 is also provided with a record medium reading device 208 such as an optical disk driver device, a floppy or flexible disk driver device and so on, and a record medium 209 readable by the record medium reading device 208, such as an optical disk, a floppy or flexible disk and so on. The record medium 209 as one example of a program storage device, tangibly embodies a program of instructions executable by the operation unit 201 to perform method steps for aiding in the preparation of a medical care schedule and record as explained in detail later with reference to flow charts of FIGS. 10 and 13. The program read by the record medium reading device 208 may be stored in the memory device 207, so as to speedily execute the program.

Nextly, each of the constitutional elements shown in FIG. 1 will be described in more detail with referring to FIGS. 1 to 9.

In FIG. 1, the communication line 2 may be an exclusive communication line constituting a LAN (Local Area Network) or an exclusive communication line of other types. For example, the communication line 2 may be a line of wire-type such as a connector cable, a telephone communication line, an optical fiber cable, etc., or a line of wire-less type such as a satellite communication line.

In FIG. 1, the memory device 102 is a device for storing the medical care data, which indicate medical care actions of various types (e.g. a test, a treatment, an injection, an examination, an evaluation, a medication) and the detail medical data related to each medical care action (e.g. temperature data, blood pressure data, blood constituent data) for each patient, each date and each type of actions. The memory device 102 is preferably a known large data volume memory device such as a hard disc device, an optical disc device or the like. The medical care data stored in the memory device 102 includes the data indicating the medical care actions which have been already performed in the past and which are scheduled to be performed in the future.

Figure 2A:
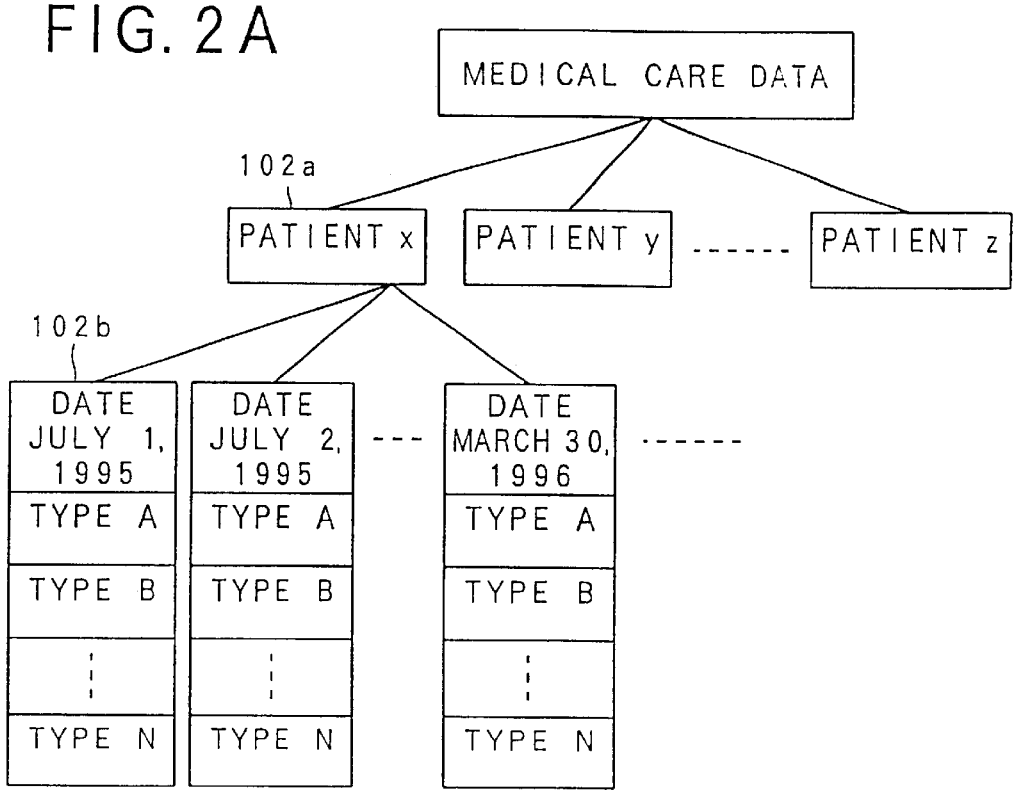
FIGS. 2 which consist of FIGS. 2A and 2B, are diagrams each showing a data structure of medical care data used in the first embodiment.
Figure 2B:
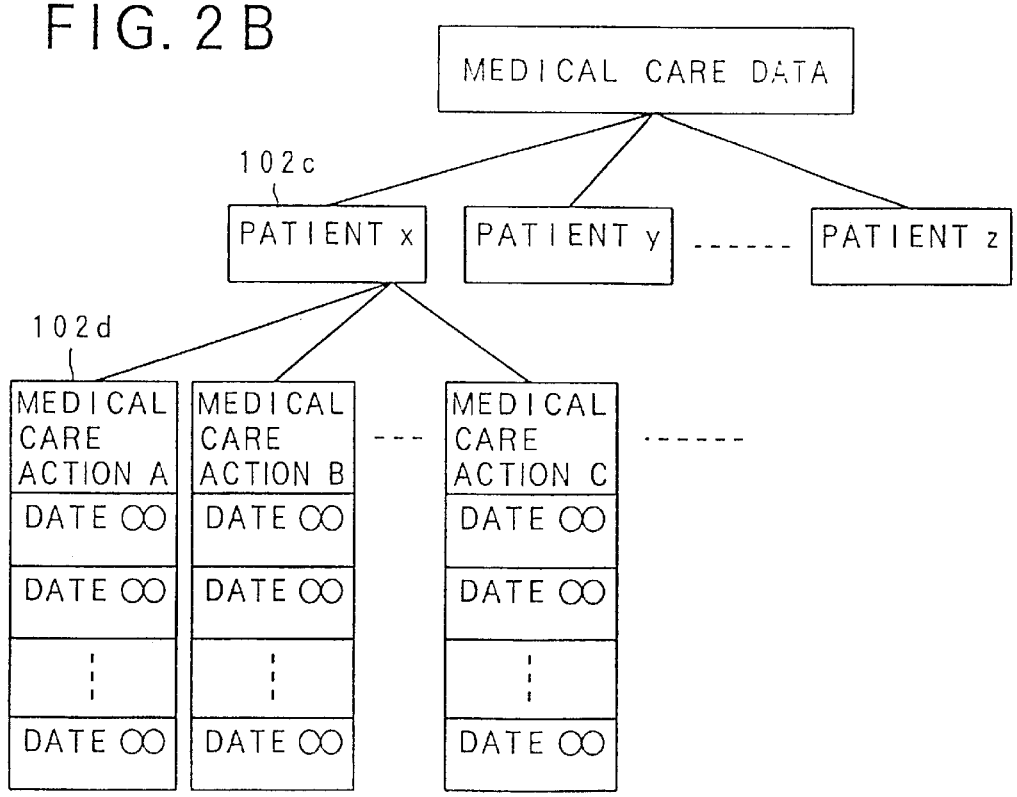

As shown in FIG. 2A, a plurality of first layer files 102a, each of which stores the medical care data for one of the patients and its accompanied detail medical data (e. g. his or her temperature data, his or her blood pressure data) are logically constituted in the memory device 102, for example. More concretely, the patient code assigned to each patient x, y, z . . . , is recorded to the header portion of the corresponding first layer file 102a. In each of the first layer files 102a, a plurality of second layer files 102b, each of which stores the medical care data and its accompanied detail medical data for each date indicated by the date data, are logically constituted. More concretely, the date code assigned to each date (e. g. Jul. 1, 1995) is recorded to the header portion of the corresponding second layer file 102b. By constituting the files in the multiple layered structure in this manner, the medical care data with respect to the patient indicated by the patient identification data can be speedily selected from the memory device 102 by the control device 104. Further, the transmission and reception of the medical care data can be performed in a data unit of the first layer file 102a by the communication devices 103 and 208 via the communication line 2, and that, the output data, which constitute the table speedily by arranging the received first layer file 102a in the order of the second layer files 102b by the control device 204, can be generated by this multiple layered structure. Alternatively, as shown in FIG. 2B, in each of the first layer files 102c, a plurality of second layer files 102d, each of which stores the medical care data and its accompanied medical data for one of the types of actions, may be logically constituted. By constituting the files logically in this manner, the selection, the transmission and the reception of the medical care data as well as the generation of the output data can be speedily performed in the same manner as the case of FIG. 2A. In the present embodiment, a result flag, which indicates whether or not each medical care action has been already performed, i.e. whether or not the detail medical data indicating the result of each medical care action exists, may be attached to each medical care data.

As shown in FIG. 3, the input device 202 is provided with: an input operation device 202a for manually inputting the patient identification data, the medical care data for each patient, each date and each type separately, and its accompanied detail medical data. In the present embodiment especially, when the detail medical data, which have been obtained as a result of the medical care action, are inputted, the result flag is set ON which indicates the fact that the pertinent medical care action has been performed. The input operation device 202a may be a known input operation device such as a key board, a ten key switch, a mouse, a track ball, an input pen, an input tablet and so on. By the input operation device 202a, each item in the table displayed on the picture plane of the display device 205 can be added, changed, modified and deleted.

In FIG. 3, in addition to the input operation device 202a, the input device 202 is also provided with a reading out device 202b for reading out the patient identification data from a record medium to which the patient identification data are recorded. As the record medium in this case, a card type medium, on which the patient identification data are magnetically, magneto-optically or optically recorded such as a magnetic card, an IC card, etc., is convenient. As the reading out device 202b, a device for magnetically, magneto-optically or optically reproducing the data in correspondence with the type of record medium is utilized.

The input device 202 is further provided with a reading out device 202c for reading out the medical care data from a record medium to which the medical care data are recorded. As the record medium in this case, a known large data volume type record medium to which the medical care data indicating the medical care actions for each patient, each date and each type of actions for example, are magnetically, magneto-optically or optically recorded such as a magnetic disc, a magneto-optical disc, an optical disc, a ROM, an IC card, a magnetic tape, etc., may be utilized. As the reading out device 202c, a device for reading the record medium magnetically, magneto-optically or optically in correspondence with the kind of record medium is utilized.

In FIG. 1 again, the communication device 203 is provided with a buffer memory, which may consist of a RAM for example, for temporarily storing the medical care data and its accompanied detail medical data in a predetermined data volume which have been sent from the center unit 101 and which are to be sent to the center unit 101. The control device 204 is adapted to generate the output data by use of the medical care data and its accompanied detail medical data transmitted from the center unit 101 and temporarily stored in this buffer memory of the communication device 203. The communication device 203 is adapted to transmit the medical care data for each patient, each date and each type of actions, which have been inputted by the input device 202, to the communication device 103 via the communication line 2. The communication device 203 is adapted to transmit the updated medical care data and its accompanied detail medical data, which have been generated by adding, changing, modifying or deleting the data on the picture plane of the display device 205 by use of the input operation device 202a, and also transmit the patient identification data and the medical care data etc. which have been inputted by the reading out devices 202b and 202c. The communication device 103 is adapted to receive the medical care data transmitted in the above explained manner, and the memory device 102 is adapted to store the medical care data and its accompanied detail medical data which have been received by the communication device 103.

In FIG. 1, the operation unit 201 is provided with the memory device 207 for storing the format information which indicates a plurality of different formats for graphically outputting the medical care data and its accompanied detail medical data, including the format which prescribes the framework of the table. The input device 202 is adapted to specify one of the formats indicated by this format information.

The control device 204 is adapted to generate the output data for graphically outputting the medical care data by the format specified by the input device 202. Particularly, the control device 204 generates the output data for graphically outputting the table having a column (i. e. a vertical row) divided into each date and a line (i. e. a horizontal row) divided into each type of the medical care actions, on the basis of the received medical care data and the format information, which are stored in the memory device 207 and which indicates the framework of the table, when the desired format of the table is specified by the input device 202.

More concretely, for example, the control device 204 firstly exchanges the medical care data, which have been received by the communication device 203, have the format for communication and include various data (e. g. the code data such as character code data, control code data or the like, the image data such as drawing data, the numerical data etc.) to the intermediate data, which can be easily developed to bit map data. Outline data, which indicate the outline of each character, mark, sign etc., partial bit-map data, which correspond to each frame of the table and the like may be employed here as the intermediate data. On the other hand, the control device 204 reads out the format information, which prescribes the framework of the table to be graphically outputted, from the format information storing area of the memory device 207. Then, the control device 204 calculates the data volume in each frame in case of making the table by use of this format according to the data volume of the medical care data converted in the intermediate data as for each type and each date, so as to determined the size of each frame of the table. Further, the control device 204 calculates the font size of the character, the mark, the sign etc. which are to be displayed or printed in each frame, and determines the displayed or printed position of the character, the mark, the sign etc., in each frame. At this time, the output data may be generated so as to display and print the character, the marks, the sign etc., by use of one constant font size all over the table or various font sizes for each frame or for each character in one table. The output data may be generated for each frame independently such that a relatively small font size is used with respect to one frame in which the number of characters to be displayed or printed is relatively large while a standard font size is used with respect to another frame in which the number of characters to be displayed or printed is relatively small. Furthermore, such an adjustment may be added to the intermediate data that the characters to be displayed or printed are partially omitted with respect to a frame in which the number of characters to be displayed is vary large, according to a predetermined standard which prescribes the content to be displayed or printed and the content to be omitted on the display or print.

After the control device 204 determines the font size and position corresponding to the intermediate data (medical care data) to be displayed or printed with respect to the framework of the specified table in the above explained manner, the control device 204 develops the intermediate data to the bit map data, which can be immediately outputted by the display device 205 and/or the printer 206, on the based on the determined font size, the determined font position and the format information indicating the framework of the table. Namely, the control device 204 bit-map-develops the intermediate data for one table onto the image data memory area of the memory device 207 or onto the output buffer in the display device 205 or the printer 206 by the unit of one table. Here, if the outline data are used as the intermediate data, the magnification of the display and printed character, mark, etc., can be freely changed with respect to the arbitrarily size of the framework, which is very convenient. If the outline data are not used but the font data are used here, which have only several predetermined kinds of font sizes, as the intermediate data, the construction and process of the control device 204 can be simplified.

When the output data are generated by the control device 204 in the above explained manner, the display device 205, which may consist of a CRT display device, a LCD device, etc., and the printer 205, which may consist of a laser beam printer, an ink jet printer etc., output a table 10 as shown in FIG. 4, for example.

In FIG. 4, the table 10 has a plurality of lines (horizontal rows) 11, which are divided into each type of medical care actions, and a plurality of columns (vertical rows) 12, which are divided into each date. The medical care actions of various types consisting each line 11, may be the record by the doctor or nurse, the process, the injection, the examination, the test, the evaluation, the medication, the meal (food), the practice, the monitor, the treatment, the activity restriction, the observation, the rehabilitation, the coordination, the hospitalization and the leave of hospital, the education for the family of the patient and so on. As for those items of medical care activities, an arbitrary item can be set depending upon the usage condition of the operator unit 201. Since various formats each of which has a possibility to be used are stored in the memory device 207 of FIG. 1 in advance, the desired one of the formats can be selected, which is very convenient. This selection of the format may be performed by displaying a menu for format selection on the display device 205. In this case, as the medical care data indicating each medical care action may be text data in which each medical care action is expressed by the text in certain language, or specific code data in which each medical care action is coded according to a predetermined rule. Especially, the medical care data, which indicate the record of the doctor or the record of the nurse, may include the text data indicating the pathobiology of the patient by the text, or the code data indicating the pathobiology of the patient by the specific code according to the predetermined rule, and further, the data in which the medical care result are expressed by the text or code data.

As shown in FIG. 4, the record of the doctor and the record of the nurse, which are recorded conventionally on different ledgers, can be displayed or printed on the same display picture plane or the same printed sheet, so that the canalization of the intentions and the team work between the doctor and the nurse can be promoted.

In the present embodiment, although the detail medical data indicating the detail record related to the medical care action of "record" in the table of FIG. 4 are not seen on the table, the detail medical data are stored in the memory device 207 in a form of hanging from the displayed medical care data in the logical data structure. For example, by clicking the mouse of the input operation device 202a of FIG. 3 on the picture plane of the display device 205 at a display position in a certain frame of the table of FIG. 4, the detail medical data corresponding to the item in the frame are displayed in the format different from this. Then, a time stamp is stamped to the medical care data and its accompanied detail medical data related to the "record" in the record of FIG. 4 each time when recording is performed by the doctor or the nurse. Namely, the date and the time of recording are recorded as the detail medical data. Thus, the doctor and the nurse can share the information in a conversation manner by use of the table.

The input device 202 is adapted to add, change, modify and delete the output data in each frame of the table 10 when the table 10 is displayed on the display device 205. The communication device 203 is adapted to transmit the updated medical care data and its accompanied detail medical data, which are corresponding to the added, changed, modified or deleted output data, to the communication device 103 via the communication line 2 under the control of the control device 204. The memory device 102 updates the stored data content by use of the new medical care data and its accompanied detail medical data which are received by the communication device 103 under the control of the control device 104. Because of the construction as described above, a table, which has a framework as shown in FIG. 4 and which major frames are originally blanked or which include only the medical care data indicating one standard medical care schedule initialized as the default values according to the predetermined standard, is firstly displayed on the display device 205. After that, the doctor in charge etc. can newly input the data by use of the input operation device 202a, and can add, change, modify or delete the data by use of the input operation device 202a, so as to making the medical care record and schedule one item by one item, which is very convenient. Further, the medical care data displayed on the table 10 can be wholly or partially replaced by the medical care data stored in the floppy disk etc. and read out by the reading out device 202c, which indicate the medical care schedule appropriately applied to the patient in the past.

The operation unit 201 may be provided with a timer or counter for counting the date, and the display data may be generated such that the graphically outputted portion related to the date coincident with "today" is displayed in a manner different from the other graphically outputted portion, on the basis of the date counted by the timer or counter. Here, as the display and/or print in a different manner, there are display methods of displaying or printing the image different in the brightness, the color, the style, the kind of lines, the concentration, the half-tone dot meshing etc. on the picture plane or the printed sheet.

In FIG. 1, the input device 202 is adapted to specify at least one of an arbitrary date, which are included in the dates of the table displayed on the picture plane of the display device 205, and/or an arbitrary type of actions, which are included in the types of actions in the table displayed on the picture plane of the display device 205. The controller 204 is adapted to generate the output data for displaying the medical care data and its accompanied detail data, which are related to this specified one of the date and/or type, in the format different from that of the table, on the picture plane of the display device 205. Namely, the control device 204 generates the output data for displaying only some portion of the medical care data and its accompanied detail medical data, which are related to the specified data and/or type among the dates and types in the table, fully on the picture plane in a list format as shown in FIG. 5 or in a magnified manner.

The switching operation from the display of the table in FIG. 4 to the display of the list in FIG. 5 can be performed when the mouse is clicked after the cursor is moved to a desirable item (e. g. frame) in the table 10 of FIG. 4 by use of the input operation device 202a of FIG. 3. Namely, by use of the detail medical data accompanied by the medical care data corresponding to the item (e. g. frame) where the cursor is positioned on the display picture plane of FIG. 4, the list of FIG. 5 is displayed. In this case, the list of FIG. 5 may be displayed by opening a window on the table of FIG. 4. Alternatively, by omitting the display of the table shown in FIG. 4, the detail medical data display as shown in FIG. 5 or the magnified display may be directly performed.

The input device 202 is adapted to specify the number of dates to be included in one table. The controller 204 is adapted to make at least one portion of the output data, which fill one frame of the table by the font, and to set the size of the font in harmonize with the size of each frame in the table, which is determined according to the dates specified by the input device 202. Namely, for example, if 14 days are specified as the dates included in one table such as "Jul. 1st to Jul. 14th", the font size corresponding to this relatively small size of the frame is used to generate the output data. On the other hand, if 3 days are specified as the dates included in one table such as "Jul. 1st to Jul. 3rd", since the frame size is rather large, the font size corresponding to this relatively large size is used to generate the output data.

In the present embodiment, the result flag is attached to the medical care data, which indicates whether or not the medical care action indicated by the medical care data has been already performed. The control device 204 is adapted to generate the output data such that the graphically outputted portion corresponding to the medical care action, which has been already performed, and the graphically outputted portion corresponding to the medical care action, which has not been performed yet, are displayed in a manner different from each other on the basis of the result flag. For example, the action which has not been performed yet may be outputted by use of blue colored characters, while the action which has already been performed may be outputted by use of black colored characters. Further, the medical care data, which can be displayed in a special format different from that of the table e. g. the medical care data which accompanies the numerical data such as the body temperature data, the blood constituent data or the like as the detail medical data, may be outputted by use of red colored characters. Other than the color, the brightness, the styles, the kind of lines, the concentration, the half tone meshing etc. may be changed on the displayed image. In this manner, by changing the display manner in accordance with the result flag, it is easy for the operator to recognize at a moment notice whether or not there exists the detail medical data as for each medical care data and whether or not the item in the table is actually completed or is in the stage of planning, which is very convenient.

FIG. 6 shows another example of the table which can be outputted by the display device 205 and the printer 205 in the present embodiment. In this case, the memory device 102 stores at least some portion of the medical care data with respect to each time of the day in addition to the date. The control device 204 is adapted to generate the output data for graphically outputting each medical care action in the order of time of the day in each frame of the table as for at least some portion of the medical care data. Corresponding to this, the display device 205 and the printer 206 output the table 20 in which the content of each frame 21 forms a list for each time of the day as shown in FIG. 6. By this, since the medical care actions are arranged in each frame of the table in the order of time of the day, it is easy for the operator to visually recognize the medical care actions performed in one day. This is especially convenient in a case where many medical care actions to be scheduled and recorded exist in one day such as the day in the hospitalization.

Figure 7:
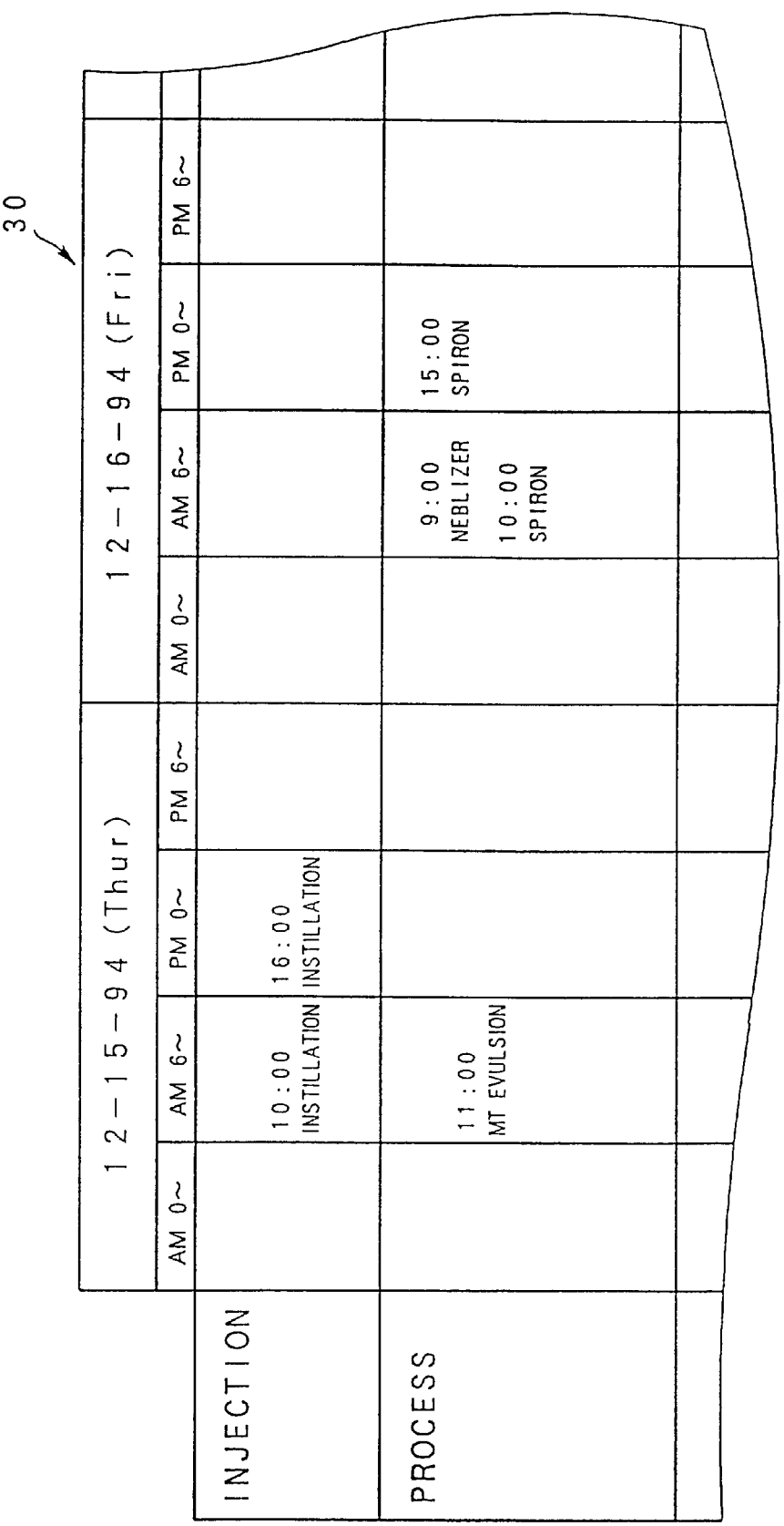
FIG. 7 is a plan view showing another example of a table which is graphically outputted by the first embodiment.

FIG. 7 shows another example of the table which can be outputted by the display device 205 and the printer 206 in the present embodiment. In this case, the memory device 102 is adapted to store at least some portion of the medical care data with respect to each time of the day in addition to the date. The control device 204 is adapted to generate the output data for graphically outputting each medical care action in a table, which columns are finely divided by a predetermined time unit in stead of just date (see FIGS. 4 and 6) in the table as for at least some portion of the medical care data. Corresponding to this, the display device 205 and the printer 206 output the table 30, in which the medical care actions in each 6 hours are put in one frame of the table and the columns are arranged every 6 hours as shown in FIG. 7. By this, if it is the case where a lot of medical care actions are to be recorded or scheduled such as the day in the hospitalization, a fine schedule for each time can be scheduled and recorded. Other than 6 hours, although a unit such as 1, 2, 3, 4, 8, or 12 hours which can easily divide 24 hours (one day) can be preferably used here, an arbitrary time unit can be used such that a time unit of long time length may be used with respect to the day time while a time unit of short time length may be used with respect to the night time. By graphically outputting the table 30 having the arrangement in the time unit, it is easy for the operator to visually recognize the medical care actions performed in one day.

Figures 8, 9:
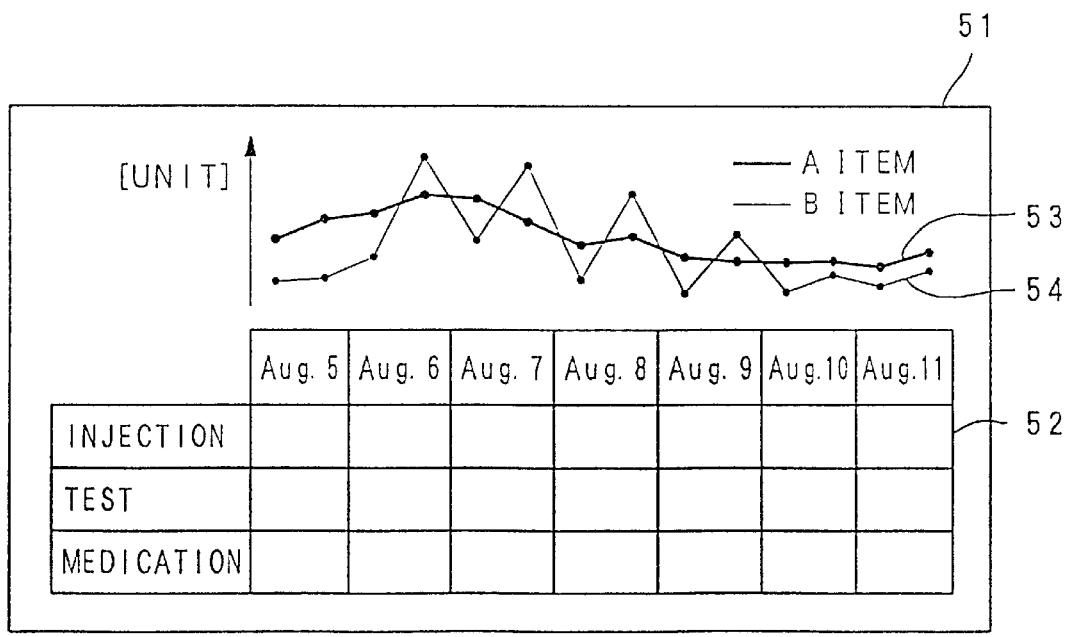
FIG. 8 is a plan view showing another example of a table which is graphically outputted by the first embodiment.
FIG. 9 is a plan view showing another example of a table which is graphically outputted by the first embodiment.

FIG. 8 shows another example of the table which can be outputted by the display device 205 and the printer 206 in the present embodiment. In this case, the control device 204 is adapted to generate the output data for graphically outputting the medical care data in a format of a table in which the medical care data are integrated by a unit of a plurality of successive dates for at least some portion of the medical care data. Corresponding to this, the display device 205 and the printer 206 output the table 40 in which the medical care actions in each one month period are put in one frame of the table and the columns are arranged ever month as shown in FIG. 8. Other than one month, although a time unit such as 3 days, one week, one year or 10 years which are easily understood, can be preferably used here, an arbitrary time unit can be used such that a short time length may be used for the time unit with respect to the period of the hospitalization while a long time length may be used for the time unit with respect to the period for the outpatient. By graphically outputting the table 40 integrating the data depending upon the frequency of the medical care actions, it is easy for the operator to visually recognize the aspect of the medical care actions in a long time span.

FIG. 9 shows another example of the table which can be outputted by the display device 205 and the printer 206 in the present embodiment. In this case the detail medical data include the numerical data related to a certain medical care action which is repeatedly recorded with respect to a plurality of dates (e. g. the body temperature, the blood pressure, the specific content concentration in the blood). The control device 204 is adapted to generate the output data for graphically outputting table 52 at one portion of the picture plane 51 of the display device 205 and at the same time graphically outputting the numerical data as a graph having the abscissa corresponding to the arrangement of the dates of the table 52 at another portion of the picture plane 51. As a result, as shown in FIG. 9, the table 52 is displayed at the lower portion of the display picture plane 51. A polygonal line graph 53 indicating the numerical data as for the A item (e.g. the body temperature) and the polygonal lime graph 54 indicating the numerical data as for the B item (e. g. blood pressure), each of which have the time axis of the date of the table 52, are displayed in the upper margin of the table 52. Accordingly, since the numerical data can be shown as the graph in correspondence with the date of the table 52, it is easy for the operator to visually recognize the relationship between the medical care actions which have been performed in the past and the numerical data which indicate the body condition etc. of the patient to which the medical care actions were applied. As shown in the example of FIG. 9, if there are several data obtained by the measurements several times in one day, by drawing the graph such that the width of each frame of the table 52, which expresses one day, is converted to 24 hours, and that the upper line of the table 52 is made corresponding to the time axis of the graph, the time relationship between the numerical data and the table 52 can be still easily recognized. On the other hand, even if the numerical data do not always exist for every date, it is still possible to draw the polygonal line graph by use of the existing data and/or by interpolating the existing data.

The format information indicating the display formats of the tables such as the tables shown in FIGS. 4 to 9 as explained above, are stored in the memory device 207 in advance, so that desirable one of them can be selected by use of the menu picture plane for selecting the format, for example.

Nextly, the operation of the present embodiment will be explained in detail. The operation explained hereinbelow is performed by the operation unit 201 in cooperation with the center unit 101, in accordance with the program of instructions to perform the method steps for aiding the preparation of medical care schedule and record, which is recorded on the record medium 209 and is read by the record medium reading device 208. The read program may be stored in the memory device 207.

First of all, the operation for referring to the table will be explained with referring to a flow chart of FIG. 10.

Figure 10:
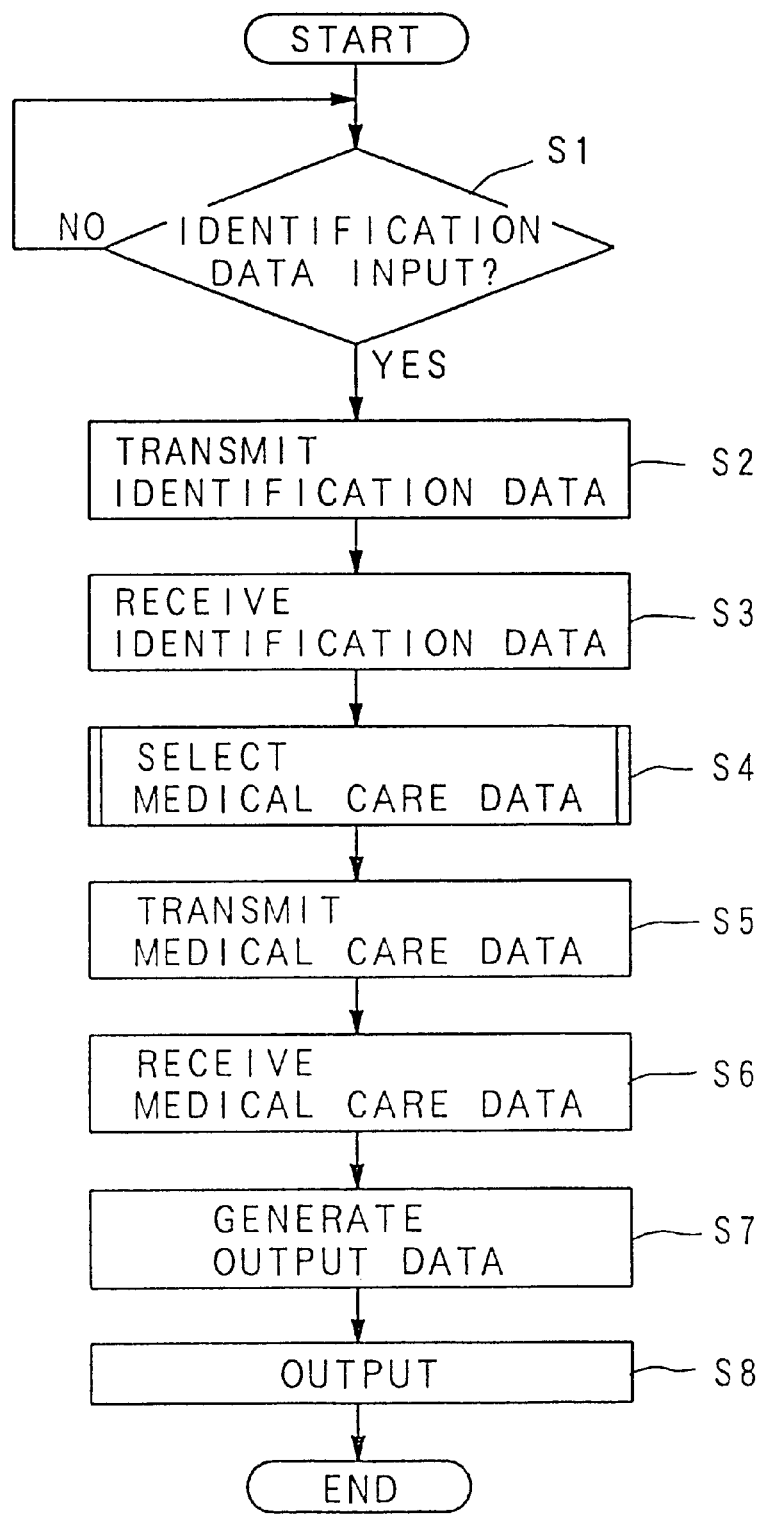
FIG. 10 is a flow chart of a referring process of the medical care navigation system of the first and second embodiments.

In FIG. 10, when the referring operation is started, on the side of the operation unit 201, it is checked by the control device 204 whether or not there is the input of the patient identification data from the input device 202 (step S1) When there is the input from the input device 202 (step S1:YES) the inputted patient identification data are transmitted from the communication device 203 via the communication line 2 (step S2). Corresponding to this, on the side of the center unit 101, the transmitted patient identification data are received by the communication device 103 via the communication line (step S3). The medical care data corresponding to the received patient identification data and its accompanied detail medical data are selected from the memory device 102 (step S4). This selection can be performed speedily by searching the header information of the file for each patient constructed in the memory device 102 as shown in FIG. 2. Nextly, the selected medical care data are transmitted from the communication device 103 via the communication line 2 (step S5). Corresponding to this, on the side of the operation unit 201, the transmitted medical care data and its accompanied detail medical data are received by the communication device 203 via the communication line 2 (step S6). The output data for graphically outputting the table are generated by the control device 204 on the basis of the received medical care data and the format information stored in the memory device 207 in advance (step S7). Finally, the output data are displayed by the display device 205 and printed out by the printer 206 (step S8), and the referring process is ended.

Nextly, the operation for inputting the medical care data will be explained with referring to a flow chart of FIG. 11.

Figure 11:
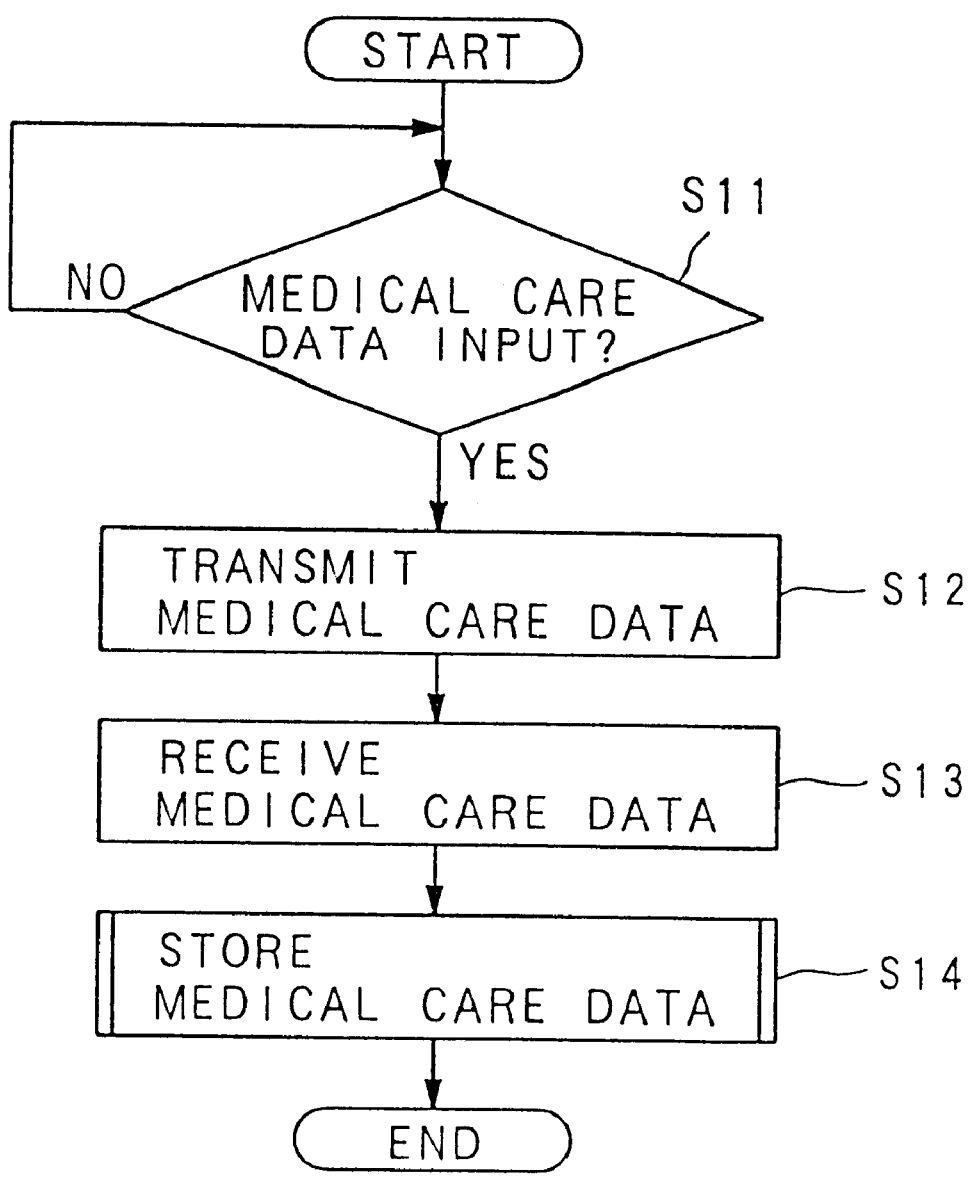
FIG. 11 is a flow chart of an inputting process of the medical care navigation system of the first and third embodiments.

In FIG. 11, when the input process is started, on the side of the operation unit 201, it is checked by the control device 204 whether or not there is the input of the medical care data and its accompanied detail medical data from the input device 202 (step S11). When there is the input from the input device 202 (step S11:YES), the inputted medical care data or detail medical data are transmitted by the communication device 203 via the communication line 2 (step S12). Corresponding to this, on the side of the center unit 101, the transmitted medical care data or detail medical data are received by the communication device 103 via the communication line 2 (step S13). The received medical care data or detail medical data are stored to the storing area for the medical care data or detail medical data for each patient and each date in the memory device 102 (step S14), and the input process is ended. This storing area in the memory device 102 can be determined speedily with respect to the files constructed in the multiple-layered structure for each patient and each date, or for each types of actions in the memory device 102 as shown in FIG. 2.

2. Second Embodiment

In a second embodiment, the input device 202 is adapted to input operator identification data for identifying an operator as well as the patient identification data in FIG. 1. The communication device 203 is adapted to transmit the operator identification data inputted by the input device 202 in addition to the patient identification data. The communication device 103 is adapted to receive the transmitted operator identification data as well as the patient identification data. The control device 104 is adapted to select only the medical care data, which correspond to the received patient identification data and which indicate the medical care action of the type set in advance as the type able to be referred to by the respective operator depending upon the operator indicated by the received operator identification data, from the memory device 102. For example, in the memory device 102, there is stored an operator table, which indicates whether or not each of the doctor, the trainee doctor, the trainee medical student, the nurse, the semi-nurse, the cook, the driver and so on is allowed to refer to the medical care data in each type of action, so that the medical care data in the type of action authorized to be referred to by the pertinent operator indicated by the received operator identification data can be speedily extracted by checking this operator table.

Nextly, the operation of the present embodiment will be explained. The operation explained hereinbelow is performed by the operation unit 201 in cooperation with the center unit 101, in accordance with the program of instructions to perform the method steps for aiding the preparation of medical care schedule and record, which is recorded on the record medium 209 and is read by the record medium reading device 208. The read program may be stored in the memory device 207.

First of all, the operation of referring to the table will be explained with referring to flow charts of FIGS. 10 and 12.

In FIG. 10, when the referring operation is started, on the side of the operation unit 201, it is checked by the control device 204 whether or not there is the input of the patient identification data and the operator identification data from the input device 202 (step S1). When there is the input from the input device 202 (step S1:YES), the inputted patient identification data and the operator identification data are transmitted from the communication device 203 via the communication line 2 (step S2). Corresponding to this, on the side of the center unit 101, the transmitted patient identification data and the transmitted operator identification data are received by the communication device 103 via the communication line (step S3). At this time, the process for selecting the medical care data in FIG. 12 is performed (step S4).

Figure 12:
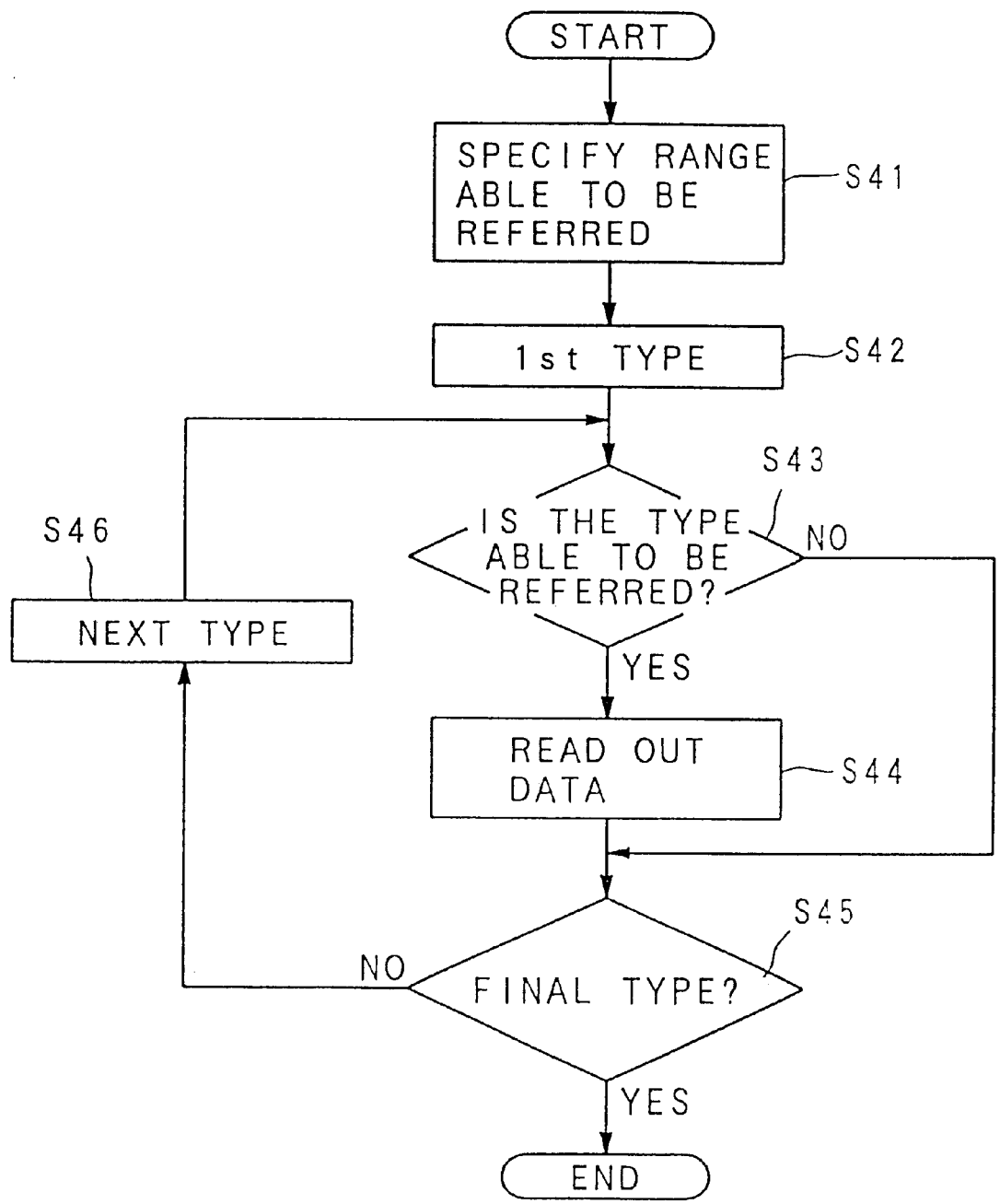
FIG. 12 is a flow chart of a selecting process in the referring process of the second embodiment.

In FIG. 12, it is judged to which occupation category (e.g. the doctor, the nurse, the pharmacist) the operator indicated by the received operator identification data belongs to, and it is also judged whether or not the operator indicated by the received operator identification data is in charge of the patient indicated by the received patient identification data, so that the range of the medical care data which are authorized and enabled to be referred to by the operator is specified (step S41). This specifying process can be speedily performed by referring to the aforementioned operator table.

Nextly, the medical care data are selected as the object for judgment, which indicate the first type of the medical care action corresponding to the patient identification data (step S42). Then, it is judged whether or not the medical care data selected as the object for judgment are authorized to be referred to by the operator on the basis of the range able to be referred to specified at the step S41 (step S43). If the type belongs to the range authorized to be referred to (step S43: YES), the medical care data and its accompanied detail medical related to this type are read out from the memory device 102 as the selected medical care data (step S44), and it is judged whether or not it is the final type of the medical care action corresponding to the received patient identification data (step S45). At the step S43, if the type does not belong to the range able to be referred to (step S43: NO), the medical care data and its accompanied detail medical data are not read out from the memory device 102 under the control of the control device 104 and the process at the step S45 are directly performed. At the step S45, if it is not judged to be the final type (step S45: NO), the same processes are performed with respect to the next type of the medical care actions corresponding to the received patient identification data (step S46 to S45). At the step S45, if it is judged to be the final type (step S45: YES), the selecting process is ended. In the above explanations, "the first type", "the next type" and "the final type" are counted by an exclusive counter by assigning numbers "1" to "n" (n: natural number) respectively to the types of the medical care actions.

In FIG. 10 again, the selected medical care data are transmitted from the communication device 103 via the communication line 2 (step S5). Corresponding to this, on the side of the operation unit 201, the transmitted medical care data and its accompanied detail medical data are received by the communication device 203 via the communication line 2 (step S6). The output data for graphically outputting the table are generated by the control device 204 on the basis of the received medical care data and the format information stored in the memory device 207 in advance (step S7). Finally, the output data are displayed by the display device 205 and/or printed out by the printer 206 (step S8), and the referring process is ended.

In this manner, according to the present embodiment, since only the medical care data and its accompanied detail medical data, which belong to the range specified as the range able to be referred to depending on the operator category in advance, can be actually referred to, the disclosure of the secret information or the infringement of the patient privacy can be efficiently prevented.

3. Third Embodiment

In a third embodiment, the input device 202 is adapted to input the operator identification data for identifying the operator together with the medical care data. The communication device 203 is adapted to transmit the operator identification data together with the medical care data inputted from the input device 202. The communication device 103 is adapted to receive the transmitted operator identification data together with the medical care data. The memory device 102 is adapted to store only the received medical care data which indicate the medical care action or actions of the type or types set in advance as the type or types authorized and enabled to be inputted by the respective operator depending upon the operator indicated by the received operator identification data. For example, in the memory device 102, there is stored an operator table, which indicates whether or not each of the doctor, the trainee doctor, the trainee medical student, the nurse, the semi-nurse, the cook, the driver and so on is allowed to input the medical care data to the memory device 102 in each type of actions, so that the medical care data in the type of action able to be inputted by the pertinent operator indicated by the received operator identification data can be speedily extracted by checking this table.

Here, the input device 202 is adapted to add, change, modify and delete the output data displayed on the picture plane of the display device 205. The communication device 203 is adapted to transmit the new medical care data corresponding to the output data, which have been added, changed, modified and deleted by the input device 202, to the center unit 101 via the communication line 2. The memory device 102 is adapted to update the content of storage by use of the received medical care data if the new medical care data received by the communication device 103 are directed to the types able to be inputted.

According to the above described second and third embodiments, the operator identification data may be inputted from the input operation device 202a of FIG. 3. Further, both of the patient identification data and the operator identification data may be inputted by the same input operation unit 202a. On the other hand, the operator identification data may be inputted from the reading out device 202b. Further, both of the patient identification data and the operator identification data may be inputted from the same reading out device 202b.

Nextly, the operation of the present embodiment will be explained. The operation explained hereinbelow is performed by the operation unit 201 in cooperation with the center unit 101, in accordance with the program of instructions to perform the method steps for aiding the preparation of medical care schedule and record, which is recorded on the record medium 209 and is read by the record medium reading device 208. The read program may be stored in the memory device 207.

First of all, the operation for inputting the medical care data will be explained with referring to flow charts of FIGS. 11 and 13.

In FIG. 11, when the input process is started, on the side of the operation unit 201, it is checked by the control device 204 whether or not there is the input of the medical care data and its accompanied detail medical data as well as the operator identification data from the input device 202 (step S11). When there is the input from the input device 202 (step S11: YES), the inputted medical care data and/or detail medical data and the operator identification data are transmitted by the communication device 203 via the communication line 2 (step S12). Corresponding to this, on the side of the center unit 101, the transmitted medical care data and/or detail medical data and the operator identification data are received by the communication device 103 via the communication line 2 (step S13).

Figure 13:
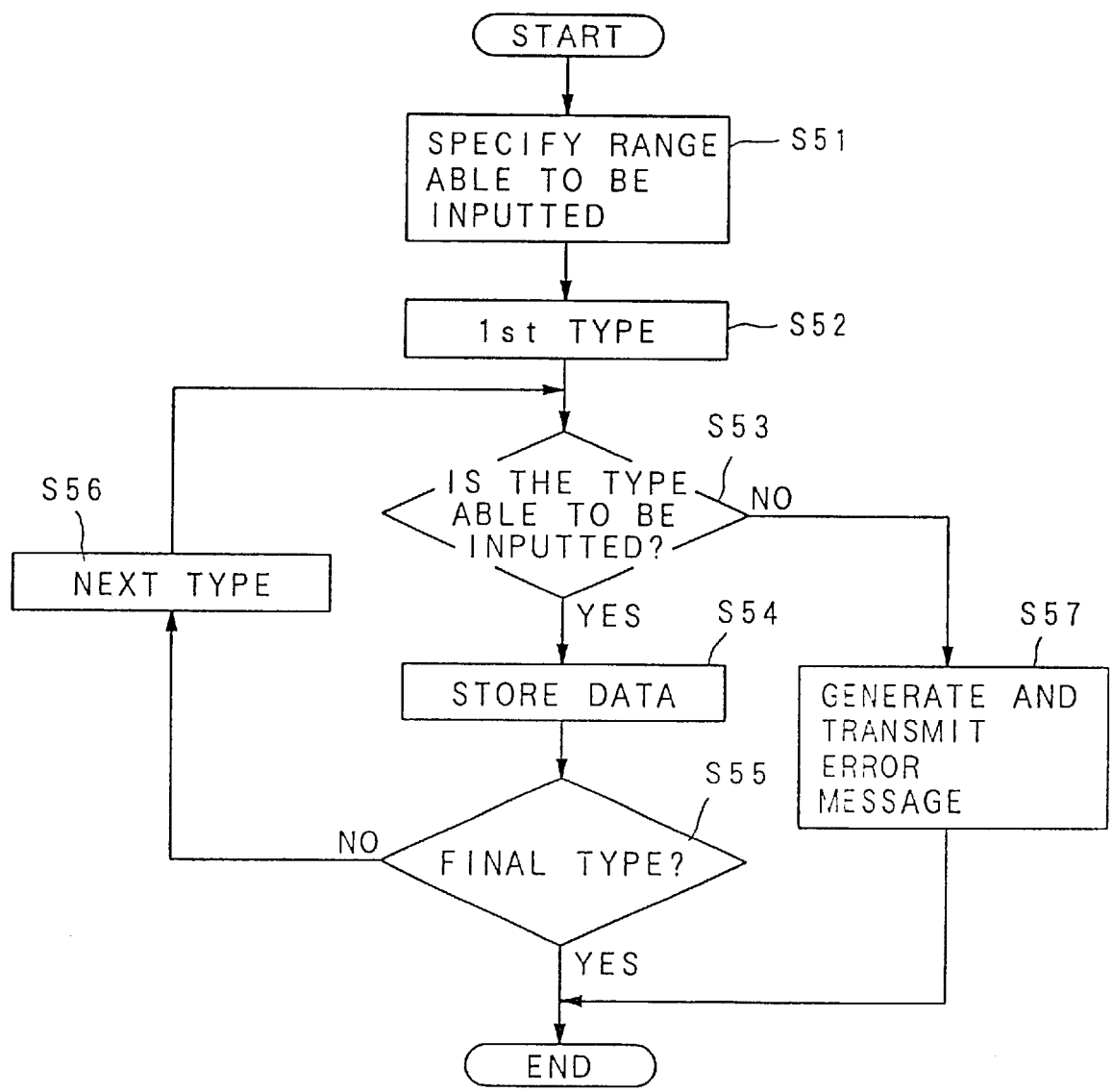
FIG. 13 is a flow chart of a storing process in the inputting process of the third embodiment.

In FIG. 13, it is judged to which occupation category (e.g. the doctor, the nurse, the pharmacist) the operator indicated by the received operator identification data belongs and it is also judged whether or not the operator indicated by the received operator identification data is in charge of the patient indicated by the patient identification data. By those judgments, the range able to be inputted by the operator is specified (step S51). This specifying process can be performed speedily by referring to the aforementioned operator table.

Nextly, the medical care data are selected as the object for judgment, which indicate the first type of the medical care action corresponding to the patient identification data (step S52). Then, it is judged whether or not the medical care data selected as the object for judgment are able to be inputted to by the operator on the basis of the range able to be inputted specified at the step S51 (step S53). If the type belongs to the range able to be inputted (step S53: YES), the medical care data and its accompanied detail medical data related to this type are stored to the memory device 102 as the updated new medical care data (step S54), and it is judged whether or not it is the final type of the medical care action corresponding to the received patient identification data (step S55). At the step S55, if it is not judged to be the final type (step S55: NO), the same processes are performed with respect to the next type of the medical care actions corresponding to the received patient identification data (step S56 to S55). At the step S55, if it is judged to be the final type (step S55: YES), the storing process is ended. In the above explanations, "the first type", "the next type" and "the final type" are counted by an exclusive counter by assigning numbers "1" to "n" (n: natural number) respectively to the types of the medical care actions.

At the step S53, if the type does not belong to the range able to be inputted (step S53: NO), the medical care data and its accompanied detail medical data related to this type are not stored to the memory device 102. Then, the control device 104 generates message data indicating an error message and transmits it from the communication device 103. Corresponding to this, the display device 205 in the operation unit 201 displays the error message such as "This item cannot be inputted by you !", so as to inform the operator of the fact that the input is prohibited for him (step S57), and the storing process is ended.

In FIG. 11 again, when the storing process is ended in this manner (step S14), the input process is ended. The storing area is determined speedily with respect to the files constructed in the multiple layered structure for each patient and each data or for each type of action in the memory device 102 as shown in FIG. 2.

The operator table which indicates the types of medical care actions able to be inputted and the types of medical care actions unable to be inputted by each operator may be set on the side of the operation unit 201 under the control of the control device 204, and, when the operator tries to input the data, the control device 204 checks whether or not the operator is able to input the data according to this operator table. Then, if the operator is not judged to be able to input, the control device 204 does not transmit the data by the communication device 203, but immediately displays an error message such as "This item is not able to be inputted by you !" and stops the inputting operation. By this, although the burden on the operation unit 201 is increased, the dead time and the dead operation of the system (e.g. the processes at the steps S12 to S14) can be diminished.

As described above, since only the medical care data and its accompanied detail medical data in the range specified as able to be inputted depending on the operator can be stored, it can efficiently prevent the erroneous data from being stored into the memory device or the medical care data which have been accumulated to construct the medical care schedule from being destroyed by human error.

Fourth Embodiment

Figure 14:
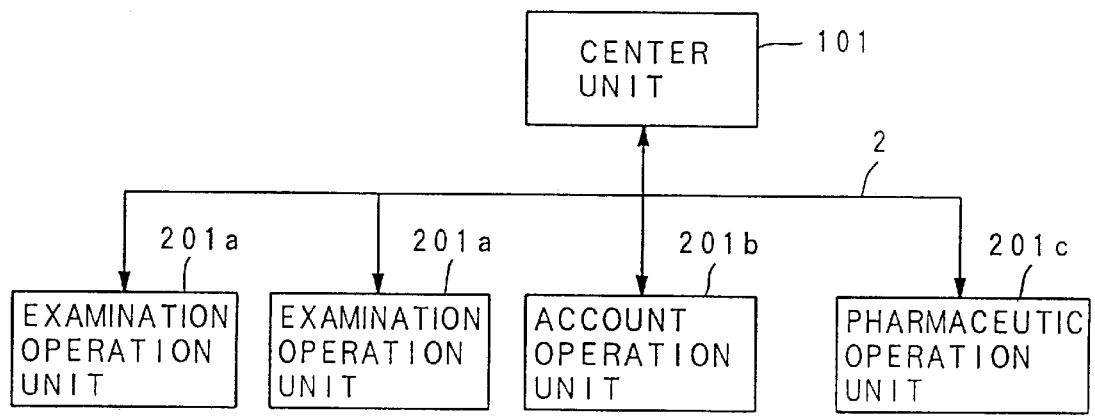
FIG. 14 is a block diagram showing a construction of a medical care navigation system of a fourth embodiment.

FIG. 14 shows a medical care navigation system in a network form as a fourth embodiment, which is provided with the center unit 101, a plurality of operation units 201a for examination areas, an operation unit 201b for accounting, and a pharmaceutic operation unit 201c connected to each other by the communication line 2.

In FIG. 14, the operation unit 201a for examination areas, as one example of the operation unit 201 in FIG. 1, is provided with the control device which has the capability of generating the output data for graphically outputting the medical care record by use of the medical care data received through the network from the center unit 101 in addition to the capability of the control device 204 in FIG. 1. The operation unit 201a for examination areas is preferably disposed at the location of each doctor. By this, each doctor can output the medical care record by the display device 205 and the printer 206 as the graphical data to explain them to the patient and his family. By switching the display picture plane, the table as shown in FIG. 4 can be displayed and printed. In this case, if there are some medical care data or its accompanied detail medical data not to be disclosed to the patient, the format to display only the data permitted to be seen by the patient can be selected from the memory device 207 and can be displayed, which is very convenient.

The operation unit 201b for accounting, another example of the operation unit 201 of FIG. 1, is provided with the control device which has the capability of performing the calculation for medical care financial records by use of the medical care data received through the network from the center unit 101 and generating the output data for graphically outputting the medical care financial record based on the calculation result in addition to the capability of the control device 204 of FIG. 1. The operation unit 201b for accounting constructed to perform the calculation of the medical point for each medical care actions and the expense for the medicine, on the basis of the kind of the insurance of each patient registered in the memory device 207 etc., and is preferably disposed at the location of the official workers in the accounting section. In this case, the operation unit 201a for examination areas may be provided with an order device for ordering the operation unit 201b for accounting to perform the calculation of the medical care account via the network.

By this, the patient, who has just finished an examination, can his account speedily updated.

The pharmaceutic operation unit 201c, as another example of the operation unit 201 of FIG. 1, is provided with the control device capable of generating the output data for graphically outputting a medicine list by use of the received medical care data, in addition to the capability of the control device 204 of FIG. 1. In this case, the operation unit 201a for examination areas may be provided with an order device for ordering the pharmaceutic operation unit 201c to graphically output the medicine list via the network. By this, the patient, who has just finished the examination, can be presented with prescribed medicine speedily.

Fifth Embodiment

In the medical care navigation systems in the above described embodiments, the center unit 101 is provided with the memory device 102 of large data volume storing type while each of the operation units 201 is a unit for individual usage which is rather simply constructed without the memory device 102 of large data volume storing type. The medical care navigation system is provided with a plurality of computer units of the same type.

Figure 15:
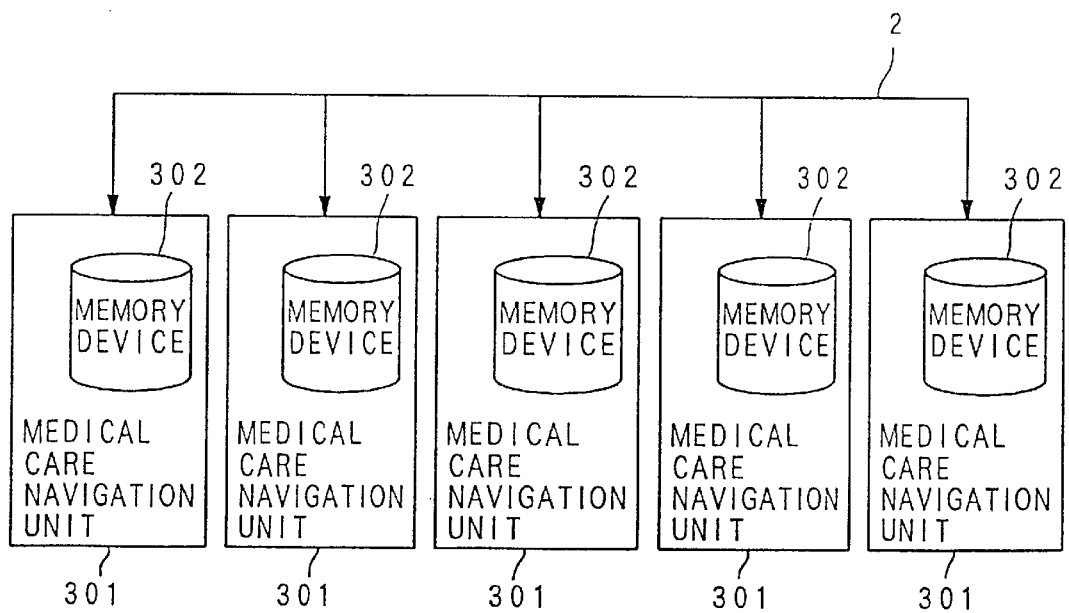
FIG. 15 is a block diagram showing a construction of a medical care navigation system of a fifth embodiment.

Namely, as shown in FIG. 15, each of medical care navigation units 301 is provided with a memory device 302 of large data volume storing type in addition to the communication device, the control device, the display device and the printer in the construction of the operation unit 201 of FIG. 1.

In this construction, it is not convenient if the contents of the medical care schedule displayed or printed in each of the navigation units 301 differ after newly inputting, modifying and deleting the medical care data at each of navigation units 301. Therefore, in order to make all of the medical care data coincident to each other in all of the memory devices 302, each time when the new medical care data are inputted at each navigation unit 302, or each time when the data are added, changed, modified and deleted, the new medical care data are transmitted and received by the communication device in each of the navigation units 301, so that the stored content of each memory device 302 are updated by the received medical care data. However, the stored content of each memory device 302 may be unified to the new medical care data periodically e.g. at a time of opening or closing the work ever day, or may be unified to the medical care data inputted at one navigation unit 201, which is predetermined to have the priority.

Finally, the function of the medical care navigation systems used in the above described embodiments are conceptually indicated in FIG. 16.

In FIG. 16, the function of the medical care navigation system 1 unifies: a function of "operation on the picture plane" 3 realized by the display device 205, the input device 202 etc. shown in FIG. 1; a function of "display" 4 realized by the display device 205 etc., a function of "various system interface" 5 realized by the communication device 203, the control device 204 etc. The function of "operation on the picture plane" 3 unifies a function of "new input" 3a, a function of "add/modify input" 3b and a function of "delete" 3c. The function of "display" 4 unifies a function of "displaying the table" 4a by use of the medical care data, a function of "displaying the result" 4b by use of the medical care data and/or the detail medical data, a function of "displaying the graph" 4c for displaying the graph by use of the detail medical data, and a function of "magnification change" 4d for changing the magnification of picture plane of the display device 205. Further, the functions of "various system interfaces" 5 unifies a function of "various order" 5a for sending an order between each medical care navigation units, a function of "electronic clinical chart" 5b used by the operation unit for medical examination, and a function of "medical account" 5c used by the operation unit for account. In this manner, since the functions are unified in the multiple layered structure, each function can be efficiently called and mutual functions organically combined to each other can be performed by the navigation system 1, which is convenient.

As described above in detailed, according to the present embodiments, since all of the staffs in the hospital can simultaneously see the same table, they can share the information as for the condition of the patient. Further, it is possible for each staff to suitably while watching the table, and suitably input the result data indicating the result of the medical care actions performed in accordance with the table while watching the table. Therefore, the medical care schedule which is the most suitable for each patient can be accumulated to be constructed in the memory device by the continuous data input operation of each staff i.e. by the team work of the whole staff in the hospital, while adding some suitable adjustment toward the medical care object such as the cure of the sickness or disease. The medical care data and its accompanied detail medical data, which construct the medical care schedule in this manner, can be reserved as the record in the strict format. Further more, since the types of medical care actions able to be referred to and the types of medical care actions able to be inputted by respective staffs are predetermined in advance, it is possible to prevent the secret information form being inadvertently disclosed and prevent the schedule from being erroneously made or being destroyed.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A medical care schedule and record aiding system comprising:

an inputting device for inputting patient identification data which indicate one of a plurality of patients;

an output data generating device for generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and an outputting device for graphically outputting the generated output data, said inputting device being constructed to input the medical care data with respect to each patient, each date and each type of the medical care action, said outputting device comprising a displaying device having a picture plane for displaying the generated output data, said inputting device being constructed to specify at least one of an arbitrary date included in a plurality of dates indicated by the output data displayed on the picture plane and an arbitrary type included in a plurality of types indicated by the output data displayed on the picture plane, said output data generating device generating the output data for displaying the medical care data related to said at least one of the date and type specified by said inputting device, in a format different from that of the table, on the basis of the format information corresponding to the different format.

2. A system according to claim 1, further comprising a format information storing device for storing format information, which prescribes a plurality of formats for graphical output and which includes the predetermined format information prescribing the framework of the table, said inputting device being constructed to specify one of the plurality of formats, said output data generating device generating the output data for graphically outputting the medical care data by the format specified by said inputting device, on the basis of the format information corresponding to the specified format.

3. A system according to claim 1, wherein said inputting device is constructed to add to, change, modify and delete the output data displayed on the picture plane of said displaying device.

4. A medical care schedule and record aiding system comprising:

an inputting device for inputting patient identification data which indicate one of a plurality of patients;

an output data generating device for generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and an outputting device for graphically outputting the generated output data, said inputting device being constructed to input the medical care data with respect to each patient, each date and each type of the medical care action and to specify the number of dates to be included in one table outputted from said outputting device, said output data generating device constituting at least a portion of the output data to fill each frame of the table by a font, and harmonizing the size of the font to a size of each frame of the table, which is determined by the number of dates specified by said inputting device.

5. A system according to claim 1, wherein said outputting device comprises a reading out device for reading out the patient identification data from a record medium to which the patient identification data are recorded.

6. A system according to claim 1, wherein said inputting device comprises a reading out device for reading out the medical care data from a record medium to which the medical care data are recorded.

7. A system according to claim 1, wherein the table comprises a plurality of columns divided by each date and a plurality of lines divided by each type of the medical care action.

8. A system according to claim 1, wherein the types of the medical care actions comprise at least one of a medical cure, a treatment, an injection, an examination, a test, an evaluation, a medication, a meal, an activity restriction, an observation, a rehabilitation, a coordination, a hospitalization, leaving a hospital, an education for a family of the patient, a record of a doctor and a record of a nurse.

9. A system according to claim 1, wherein said system comprises a unit for medical examination and said output data generating device generates the output data for graphically outputting a medical examination report by use of the medical care data.

10. A system according to claim 1, wherein said system comprises an accounting unit and said output data generating device further performs a calculation for medical care account by use of the medical care data and generating the output data for graphically outputting a medical care account record on the basis of a calculation result.

11. A system according to claim 1, wherein said system comprises a pharmaceutic unit and said output data generating device generates the output data for graphically outputting a medicine list by use of the medical care data.

12. A system according to claim 1, wherein said output data generating device generates the output data for graphically outputting the medical care data in a format of a table in which the medical care actions are arranged in the second rows for each predetermined consecutive dates, as for at least one portion of the medical care data.

13. A system according to claim 1, further comprising: a medical care data storing device for storing the medical care data; and a selecting device for selecting the medical care data related to the patient indicated by the inputted patient identification data.

14. A system according to claim 13, wherein said medical care data storing device updates its stored content by new medical care data inputted by said inputting device.

15. A system according to claim 13, wherein said inputting device is constructed to input operator identification data for identifying an operator in addition to the patient identification data, said selecting device selecting only the medical care data indicating the medical care action of a type, which is predetermined as a type able to be referred to with respect to the operator indicated by the inputted operator identification data, as for the patient indicated by the inputted patient identification data.

16. A system according to claim 13, wherein said inputting device is constructed to input operator identification data for identifying an operator in addition to the medical care data, said medical care data storing device storing only the inputted medical care data indicating the medical care action of a type which is predetermined as a type able to be inputted with respect to the operator indicated by the inputted operator identification data.

17. A system according to claim 13, wherein said medical care data storing device stores at least one portion of the medical care data for each time of the day in addition to the date, said output data generating device generating the output data for graphically outputting the medical care data such that the medical care actions are arranged per each time of the day in each frame of the table as for said at least one portion of the medical care data, on the basis of the medical care data for each time of the day.

18. A system according to claim 13, wherein said medical care data storing device stores at least one portion of the medical care data for each time of the day in addition to the date, said output data generating device generating the output data for graphically outputting the medical care data such that the medical care actions are arranged in the table divided into each predetermined time interval, as for said at least one portion of the medical care data, on the basis of the medical care data for each time of the day.

19. A medical care schedule and record aiding system comprising:

an inputting device for inputting patient identification data which indicate one of a plurality of patients;

an output data generating device for generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and an outputting device for graphically outputting the generated output data, said inputting device being constructed to input the medical care data with respect to each patient, each date and each type of the medical care action, said system further comprising a counter for counting the date, said output data generating device generating the output data such that one portion of graphical output related to the date corresponding to a present day is displayed in a display manner different from that of the other portion of graphical output, on the basis of the date counted by said counter.

20. A medical care schedule and record aiding system comprising:

an inputting device for inputting patient identification data which indicate one of a plurality of patients;

an output data generating device for generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and an outputting device for graphically outputting the generated output data, said inputting device being constructed to input the medical care data with respect to each patient, each date and each type of the medical care action, wherein a result flag indicating whether or not the medical care action has been already performed is attached to the medical care data, and said output data generating device generates the output data such that one portion of graphical output related to the medical care action which has been already performed is displayed in a display manner different from that of another portion of graphical output related to the medical care action which has not been performed yet, on the basis of the result flag.

21. A medical care schedule and record aiding system comprising:

an inputting device for inputting patient identification data which indicate one of a plurality of patients;

an output data generating device for generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and an outputting device graphically outputting the generated output data, said inputting device being constructed to input the medical care data with respect to each patient, each date and each type of the medical care action, and to specify desirable one of the medical care data among the medical care data outputted as the table by said outputting device, said output data generating device generating the output data for graphically outputting detail medical data related to said desirable one of the medical care data specified by said inputting device from among the detail medical data related to the medical care action indicated by each medical care data, in connection with each medical care date, in a predetermined format different from that of the table, on the basis of the detail medical data, the detail medical data including numerical data, which are related to a predetermined type of the medical care action and are recorded with respect to a plurality of dates, said output data generating device generating the output data for graphically outputting the table at one portion of an output image and further generating the output data for graphically outputting the numerical data as a graph having a time axis corresponding to an arrangement of the dates of the table at another portion of the output image on the basis of the numerical data.

22. A program storage device readable by a medical care schedule and record aiding apparatus, tangibly embodying a program of instructions executable by the medical care schedule and record aiding apparatus to perform method steps for aiding a preparation of medical care schedule and record, said method steps comprising:

inputting patient identification data which indicate one of a plurality of patients;

generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and graphically outputting the generated output data, wherein, in said inputting step, the medical care data is inputted with respect to each patient, each date and each type of the medical care action, in said generating step, the output data is generated to be displayed by a displaying device having a picture plane, said method steps further comprising specifying at least one of an arbitrary date included in a plurality of dates indicated by the output data displayed on the picture plane and an arbitrary type included in a plurality of types indicated by the output data displayed on the picture plane, and in said generating step, the output data for displaying the medical care data related to said at least one of the date and type specified by said inputting step, in a format different from that of the table, is generated on the basis of the format information corresponding to the different format.

23. A program storage device readable by a medical care schedule and record aiding apparatus, tangibly embodying a program of instructions executable by the medical care schedule and record aiding apparatus to perform method steps for aiding a preparation of medical care schedule and record, said method steps comprising:

inputting patient identification data which indicate one of a plurality of patients;

generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and graphically outputting the generated output data, wherein, in said inputting step, the medical care data is inputted with respect to each patient, each date and each type of the medical care action, said method steps further comprising specifying the number of dates to be included in one table outputted by said graphically outputting step, and in said output data generating step, at least a portion of the output data to fill each frame of the table is constituted by a font, and the size of the font is harmonized to a size of each frame of the table, which is determined by the number of dates specifically by said specifying step.

24. A program storage device readable by a medical care schedule and record aiding apparatus, tangibly embodying a program of instructions executable by the medical care schedule and record aiding apparatus to perform method steps for aiding a preparation of medical care schedule and record, said method steps comprising:

inputting patient identification data which indicate one of a plurality of patients;

generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and graphically outputting the generated output data, wherein, in said inputting step, the medical care data with respect to each patient, each date and each type of the medical care action is inputted, said method steps further comprise counting the date, in said output data generating step, the output data is generated such that one portion of graphical output related to the date corresponding to a present day is displayed in a display manner different from that of the other portion of graphical output, on the basis of the date counted by said counting step.

25. A program storage device readable by a medical care schedule and record aiding apparatus, tangibly embodying a program of instructions executable by the medical care schedule and record aiding apparatus to perform method steps for aiding a preparation of medical care schedule and record, said method steps comprising:

inputting patient identification data which indicate one of a plurality of patients;

generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and graphically outputting the generated output data, wherein, in said inputting step, the medical care data with respect to each patient, each date and each type of the medical care action is inputted, said method steps further comprise attaching a result flag indicating whether or not the medical care action has been already performed to the medical care data, and in said output data generating step, the output data is generated such that one portion of graphical output related to the medical care action which has been already performed is displayed in a display manner different from that of the another portion of graphical output related to the medical care action which has not been performed yet on the basis of the result flag.

26. A program storage device readable by a medical care schedule and record aiding apparatus, tangibly embodying a program of instructions executable by the medical care schedule and record aiding apparatus to perform method steps for aiding a preparation of medical care schedule and record, said method steps comprising:

inputting patient identification data which indicate one of a plurality of patients;

generating output data to be graphically outputted in a format of a table, in which medical care actions indicated by medical care data related to the patient indicated by the inputted patient identification data among the medical care data which indicate a plurality of types of the medical care actions with respect to each of the plurality of patients and each date respectively are arranged in first rows for each type of the medical care actions and in second rows orthogonal to said first rows for each date, on the basis of a predetermined format information, which prescribes a framework of the table, and the medical care data related to the patient indicated by the inputted patient identification data; and graphically outputting the generated output data, wherein, in said inputting step, the medical care data with respect to each patient, each date and each type of the medical care action is inputted, and desirable one of the medical care data among the medical care data outputted as the table by said graphically outputting step is specified, in said output data generating step, the output data for graphically outputting detail medical data related to said desirable one of the medical care data specified by said inputting step from among the detail medical data related to the medical care action indicated by each medical care data, in connection with each medical care date, in a predetermined format different from that of the table, is generated on the basis of the detail medical data, and the detail medical data include numerical data, which are related to a predetermined type of the medical care action and are recorded with respect to a plurality of dates, in said output data generating step, the output data for graphically outputting the table at one portion of an output image is generated and the output data for graphically outputting the numerical data as a graph having a time axis corresponding to an arrangement of the dates of the table at another portion of the output image is further generated on the basis of the numerical data.

* * * * *